(12) United States Patent
Borgstahl et al.

(10) Patent No.: US 6,498,829 B1
(45) Date of Patent: Dec. 24, 2002

(54) METHOD FOR MEASUREMENT OF PHYSICAL CHARACTERISTICS OF CRYSTALS

(75) Inventors: Gloria E. O. Borgstahl, Toleda, OH (US); Jeffrey J. Lovelace, Rossford, OH (US); Edward H. Snell, Huntsville, AL (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 09/894,511

(22) Filed: Jun. 28, 2001

(51) Int. Cl.$^7$ ............................................. G01N 23/207
(52) U.S. Cl. ........................................................ 378/73
(58) Field of Search ..................... 378/71–81

(56) References Cited

PUBLICATIONS

Bellamy et al., The high–mosaicity illusion: revealing the true physical characteristics of macromolecular crystals, Acta Cryst. (2000), D56, pp 986–995.
Lovelace et al., Computer program abstracts, J. Appl. Cryst. (2000) 33, pp 1187–1188.
Snell et al., Investigating the Effect of Impurities on Macromolecule Crystal Growth in Microgravity, Crystal Growth & Design (2001), vol. 1, No. 2, pp 151–158.
Baker, E.N., et al. (1988) *Phil Trans. R. Soc. Lond.*, B319, 368–456.
Boggon, T.J., et al. (2000) *Acta Cryst.*, D56, 868–880.
Borgstahl, et al. (2000), *J. Mol. Biol.*, 296, 951–959.
Chayen, N.E., et al. (1997), *J. Cryst. Growth*, 171, 219–225.
Ciszak, E., et al. (1994), *Biochemistry*, 33, 1512–1517.
Colapietro, M., et al. (1992), *J. Appl. Cryst.*, 25, 192–194.
Collaborative Computational Project, No. 4 (1994), *Acta Cryst.*, D50, 760–763.
Darwin, C.G. (1922), *Philios. Mag.*, 43, 800–829.
Evans, P.R. (1997), In Proceedings of the CCP4 Study Weekend. *Recent Advances in Phasing*, edited by K.S. Wilson, G. Davies, A.W. Ashton & S. Bailey. Warrington: Daresbury Laboratory.
Ferrer, J.L., et al. (1998), *J. Appl. Cryst.*, 31, 523–532.
Fourme, R., et al. (1995) *J. Synchrotron Rad.*, 2, 136–142.
Greenhough, T.J., et al. (1982), *J. Appl. Cryst.*, 15, 338–351.
Helliwell, J.R. (1988), *J. Cryst. Growth*, 90, 259–272.
Kabsch, W. (1988), *J. Appl. Cryst.*, 21, 916–924.
Leslie, A.G.W. (1999) *Acta Cryst.*, D55, 1696–1702.
Long, M.M., et al. (1996), *J. Crystal Growth*, 168, 233–243.
Margaritondo, G. (1995), *J. Synchrotron Rad.*, 2, 148–154.
Nave, C. (1998), *Acta Cryst.*, D54, 848–853.
Nave, C. (1999), *Acta Cryst.*, D55, 1663–1668.
Ng., J.D., et al. (1997), *Acta Cryst.*, D53, 724–733.
Powell, H.R. (1999), *Acta Cryst.*, D55, 1690–1695.
Pusey, M.L., et al. (1986), *J. Cryst. Growth*, 76, 593–599.
Pusey, M., et al. (1988), *J. Cryst. Growth*, 90, 105–111.
Shaikevitch, A., et al. (1981), *Acta Cryst.*, A37, 871–875.
Shen, Q., et al. (2000), *Acta Cryst.*, A56, 268–279.
Snell, E.H., et al. (1995), *Acta Cryst.*, D51, 1099–1102.
Snell, E.H. (1998), Proceedings of the Spacebound 1997 Meeting, pp. 306–315, Canadian Space Agency.
Snell, E.H., et al. (1997), *Acta Cryst.*, D53, 231–239.
Steller, I., et al. (1997), *J. Appl. Cryst.*, 30, 1036–1040.
Wang, B.C. (1985), *Methods in Enzymol.*, 115, 90–112.
Weckert, E., et al. (1997), *Acta Cryst.*, A53, 108–143.

*Primary Examiner*—Craig E. Church
(74) *Attorney, Agent, or Firm*—Emch, Schaffer, Schaub & Porcello, Co., L.P.A.

(57) ABSTRACT

A method and apparatus to simultaneously measure the diffraction resolution and mosaic spread of macromolecular crystals, are described. The method includes minimizing contributions of an x-ray beam to any reflection angular widths in the crystal, rapidly measuring multi reflection profiles in the crystal over a wide resolution range, evaluating and deconvoluting the Lorentz effect and beam contributions, and determining the direction in which the crystal is most perfect.

33 Claims, 16 Drawing Sheets

(2 of 16 Drawing Sheet(s) Filed in Color)

Fig. 4 (Table 1)

| Ring | Sec. | $h_{min} \to h_{max}$ | $k_{min} \to k_{max}$ | $l_{min} \to l_{max}$ | No. ref. | $\eta$ FWHM | $\eta$ FWQM | $\eta$ Gaussian fit 1 | $\eta$ Gaussian fit 2 | Peak areas (% total area) Fit 1 | Fit 2 |
|---|---|---|---|---|---|---|---|---|---|---|---|
| 0 | 0 | | | | 0 | | | | | | |
| 1 | 0 | 3→4 | 7→10 | 14→19 | 2 | 11.4 (0.4) | 15.7 (0.8) | 5.2 (0.1) | 8.1 (0.8) | 48 (10) | 42 (1) |
| 2 | 0 | −2→5 | 4→15 | 23→40 | 9 | 8.3 (1.8) | 12.5 (2.8) | 5.0 (1.5) | 5.5 (1.7) | 56 (7) | 35 (12) |
| 3 | 0 | −3→5 | 5→17 | 35→48 | 6 | 8.7 (2.4) | 12.5 (3.4) | 4.9 (2.0) | 5.8 (2.0) | 56 (13) | 35 (14) |
| Sec. 0 total | | −3→5 | 4→17 | 14→48 | 17 | 8.8 (2.1) | 12.9 (3.0) | 5.0 (1.6) | 5.9 (1.9) | 55 (10) | 36 (12) |
| 0 | 1 | 2 | 4 | 6 | 1 | 11.3 | 17.4 | 5.9 | 7.4 | 57 | 36 |
| 1 | 1 | 4→7 | 8→15 | 2→9 | 6 | 13.5 (0.9) | 18.5 (0.7) | 6.5 (0.7) | 8.2 (1.5) | 55 (3) | 38 (8) |
| 2 | 1 | 5→10 | 13→22 | 1→26 | 18 | 13.1 (2.2) | 17.5 (2.6) | 6.1 (1.0) | 7.5 (1.7) | 54 (7) | 36 (36) |
| 3 | 1 | 7→12 | 21→32 | 1→37 | 18 | 13.3 (1.8) | 18.5 (3.7) | 6.5 (1.5) | 7.4 (2.4) | 47 (11) | 31 (11) |
| Sec. 1 total | | 2→12 | 4→32 | 1→37 | 43 | 13.2 (1.9) | 18.1 (2.9) | 6.3 (1.2) | 7.6 (1.9) | 51 (9) | 34 (9) |
| 0 | 2 | | | | 0 | | | | | | |
| 1 | 2 | 6 | 12 | −20 | 1 | 9.0 | 11.6 | 5.0 | 3.3 | 50 | 18 |
| 2 | 2 | 6→10 | 12→22 | −30→−1 | 27 | 11.8 (2.0) | 15.2 (2.7) | 6.2 (0.9) | 5.9 (1.6) | 59 (7) | 34 (8) |
| 3 | 2 | 9→12 | 21→30 | −37→−1 | 18 | 11.6 (2.6) | 14.9 (2.8) | 6.0 (1.0) | 6.0 (1.5) | 53 (9) | 34 (7) |
| Sec. 2 total | | 6→13 | 12→33 | −31→−1 | 47 | 11.6 (2.2) | 15.0 (2.7) | 6.1 (1.0) | 5.9 (1.6) | 57 (8) | 33 (8) |
| 0 | 3 | | | | 0 | | | | | | |
| 1 | 3 | 2→4 | 4→8 | −26→−24 | 3 | 4.1 (0.9) | 6.4 (1.5) | 4.4 (2.1) | 2.3 (0.7) | 59 (0) | 28 (12) |
| 2 | 3 | 1→6 | 3→14 | −42→−31 | 9 | 4.0 (1.3) | 5.9 (1.7) | 3.1 (1.0) | 3.2 (1.3) | 56 (5) | 36 (7) |
| 3 | 3 | −1→8 | 5→22 | −56→−37 | 11 | 4.1 (1.2) | 6.1 (1.8) | 3.2 (1.0) | 3.0 (1.6) | 63 (12) | 30 (11) |
| Sec. 3 total | | −1→8 | 3→22 | −56→−24 | 23 | 4.0 (1.2) | 6.1 (1.7) | 3.3 (1.1) | 3.0 (1.4) | 60 (9) | 32 (9) |
| 0 | 4 | −3→−3 | −5→−5 | −12→−11 | 2 | 10.8 (0.7) | 16.0 (0.2) | 5.6 (0.4) | 7.5 (1.2) | 55 (10) | 39 (8) |
| 1 | 4 | −5→−3 | −7→−5 | −27→−13 | 5 | 9.1 (1.0) | 13.7 (1.3) | 5.3 (0.2) | 7.0 (0.7) | 57 (7) | 36 (4) |
| 2 | 4 | −8→−4 | −10→−4 | −39→−28 | 7 | 9.0 (1.1) | 12.9 (1.1) | 5.3 (0.7) | 7.4 (1.5) | 56 (5) | 40 (4) |
| 3 | 4 | −13→−5 | −15→−3 | −51→−39 | 11 | 8.4 (1.4) | 12.2 (1.4) | 5.3 (0.6) | 6.3 (2.0) | 58 (12) | 35 (8) |
| Sec. 4 total | | −13→−3 | −15→−3 | −51→−11 | 25 | 8.9 (1.3) | 13.0 (1.6) | 5.4 (0.5) | 6.9 (1.6) | 57 (9) | 37 (7) |
| 0 | 5 | −3→−3 | −5→−5 | −10→−5 | 6 | 12.7 (1.8) | 17.5 (1.3) | 6.2 (0.4) | 8.1 (1.4) | 54 (11) | 38 (1) |
| 1 | 5 | −9→−8 | −13→−12 | −14→−2 | 11 | 13.2 (1.5) | 17.9 (1.0) | 5.9 (0.5) | 8.8 (1.7) | 53 (10) | 42 (4) |
| 2 | 5 | −13→−9 | −17→−13 | −28→−6 | 10 | 12.4 (1.0) | 17.0 (0.9) | 6.0 (0.7) | 7.3 (1.1) | 55 (8) | 37 (7) |
| 3 | 5 | −15→−13 | −19→−17 | −29→−28 | 4 | 10.2 (1.8) | 17.6 (2.4) | 6.1 (1.2) | 7.4 (1.0) | 52 (7) | 34 (11) |
| Sec. 5 total | | −15→−3 | −19→−5 | −29→−2 | 31 | 12.5 (1.7) | 17.5 (1.3) | 6.0 (0.6) | 8.0 (1.5) | 54 (9) | 39 (6) |
| 0 | 6 | | −4 | −6 | 4 | 1 | 11.6 | 16.2 | 5.3 | 8.1 | 52 | 49 |
| 1 | 6 | −10→−5 | −14→−7 | 2→18 | 7 | 9.8 (2.6) | 13.4 (3.3) | 5.2 (0.9) | 5.9 (2.1) | 55 (7) | 34 (9) |
| 2 | 6 | −15→−10 | −19→−12 | 4→26 | 23 | 11.1 (2.2) | 14.3 (2.8) | 5.6 (1.0) | 6.0 (1.6) | 58 (9) | 36 (7) |
| 3 | 6 | −22→−15 | −26→−17 | 6→38 | 18 | 10.6 (1.8) | 14.4 (2.5) | 5.6 (0.7) | 6.5 (2.0) | 55 (9) | 37 (7) |
| 4 | 6 | −21→−19 | −23→−19 | 25→37 | 2 | 9.7 (4.3) | 12.2 (4.3) | 4.3 (3.5) | 5.9 (3.5) | 51 (11) | 44 (1) |
| Sec. 6 total | | −22→−4 | −26→−6 | 2→38 | 51 | 10.7 (2.1) | 14.2 (2.8) | 5.5 (0.9) | 6.2 (1.8) | 56 (9) | 37 (7) |
| 0 | 7 | | | | 0 | | | | | | |
| 1 | 7 | −6→−3 | −6→−3 | 17→26 | 2 | 3.1 (2.9) | 4.7 (3.2) | 1.7 (2.0) | 1.8 (1.8) | 47 (15) | 28 (7) |
| 2 | 7 | −12→−7 | −12→−5 | 28→36 | 5 | 5.1 (1.1) | 6.8 (1.5) | 2.9 (0.8) | 2.8 (0.6) | 57 (6) | 36 (2) |
| 3 | 7 | −15→−8 | −15→−2 | 35→53 | 16 | 4.3 (1.9) | 7.0 (2.2) | 3.3 (1.6) | 2.9 (1.8) | 58 (11) | 30 (12) |
| Sec. 7 total | | −15→−3 | −15→−2 | 17→53 | 21 | 4.5 (1.9) | 6.8 (2.2) | 3.1 (1.5) | 2.8 (1.6) | 57 (10) | 31 (10) |
| Total | | −22→13 | −26→33 | −56→53 | 260 | 10.1 (3.6) | 13.8 (4.5) | 5.4 (1.5) | 6.1 (2.3) | 55 (9) | 35 (9) |

Fig. 6 (Table 2)

| h | k | l | d (Å) | $I_{max}$ | η FWHM | η FWQM | Ring | Sec. | Gaussian fit 1 | | | Gaussian fit 2 | | |
|---|---|---|---|---|---|---|---|---|---|---|---|---|---|---|
| | | | | | | | | | I | η FWHM | Area (%) | I | η FWHM | Area (%) |
| The strongest reflection in each sector of ring 1 | | | | | | | | | | | | | | |
| 4 | 10 | 19 | 6.8 | 1053 | 11.1 | 15.1 | 1 | 0 | 971 | 5.1 | 55 | 572 | 7.5 | 43 |
| 6 | 12 | 2 | 7.9 | 1800 | 13.8 | 17.3 | 1 | 1 | 1814 | 6.2 | 56 | 1035 | 7.8 | 39 |
| 6 | 12 | −20 | 6.0 | 146 | 9.0 | 11.6 | 1 | 2 | 131 | 5.0 | 50 | 61 | 3.3 | 18 |
| 2 | 4 | −24 | 7.2 | 2082 | 3.1 | 4.8 | 1 | 3 | 1297 | 3.0 | 59 | 845 | 2.8 | 37 |
| −3 | −5 | −14 | 10.5 | 841 | 10.3 | 15.6 | 1 | 4 | 696 | 5.0 | 48 | 441 | 8.1 | 43 |
| −8 | −12 | −8 | 7.0 | 974 | 12.5 | 17.4 | 1 | 5 | 929 | 5.6 | 55 | 529 | 9.0 | 46 |
| −7 | −9 | 16 | 7.1 | 686 | 7.9 | 11.7 | 1 | 6 | 578 | 5.3 | 59 | 288 | 5.4 | 30 |
| −3 | −3 | 17 | 9.7 | 1500 | 1.1 | 2.4 | 1 | 7 | 1286 | 0.3 | 58 | 663 | 0.5 | 32 |
| The strongest reflection in each sector of ring 3 | | | | | | | | | | | | | | |
| 1 | 11 | 43 | 3.9 | 596 | 8.9 | 12.1 | 3 | 0 | 490 | 5.4 | 60 | 275 | 7.1 | 40 |
| 8 | 22 | 27 | 3.8 | 702 | 13.3 | 16.3 | 3 | 1 | 634 | 6.1 | 53 | 376 | 7.2 | 36 |
| 11 | 25 | −10 | 3.8 | 471 | 14.5 | 18.5 | 3 | 2 | 406 | 6.9 | 48 | 281 | 8.1 | 38 |
| 7 | 17 | −37 | 3.7 | 635 | 5.1 | 8.5 | 3 | 3 | 447 | 4.6 | 63 | 254 | 5.0 | 38 |
| −9 | −11 | −39 | 3.9 | 862 | 8.8 | 12.7 | 3 | 4 | 757 | 5.2 | 61 | 416 | 6.4 | 39 |
| −13 | −17 | −29 | 3.9 | 278 | 8.8 | 15.3 | 3 | 5 | 257 | 5.9 | 61 | 125 | 7.6 | 36 |
| −17 | −21 | 11 | 3.8 | 588 | 12.6 | 17.6 | 3 | 6 | 532 | 5.6 | 44 | 362 | 8.8 | 45 |
| −13 | −13 | 36 | 3.8 | 560 | 6.1 | 7.9 | 3 | 7 | 422 | 4.7 | 65 | 303 | 2.9 | 34 |
| Symmetry-related reflections | | | | | | | | | | | | | | |
| 11 | 25 | 1 | 3.9 | 362 | 13.0 | 18.3 | 3 | 1 | 337 | 5.9 | 46 | 183 | 9.4 | 37 |
| 11 | 25 | −1 | 3.9 | 323 | 13.9 | 17.6 | 3 | 2 | 330 | 7.0 | 61 | 201 | 6.5 | 35 |
| 10 | 22 | 1 | 4.4 | 840 | 14.2 | 18.4 | 2 | 1 | 777 | 6.4 | 51 | 506 | 8.7 | 43 |
| 10 | 22 | −1 | 4.4 | 824 | 14.6 | 19.2 | 2 | 2 | 771 | 6.6 | 55 | 497 | 8.9 | 46 |
| 9 | 19 | 1 | 5.1 | 208 | 16.8 | 19.4 | 2 | 1 | 188 | 6.3 | 39 | 126 | 7.3 | 29 |
| 9 | 19 | −1 | 5.1 | 225 | 13.7 | 18.8 | 2 | 2 | 219 | 5.9 | 49 | 134 | 8.7 | 42 |

Fig. 7 (Table 3)

| h | k | l | d (Å) | $I_{max}$ | $\eta$ FWHM | $\eta$ FWQM | Ring | Sec. | Gaussian fit 1 | | | Gaussian fit 2 | | |
|---|---|---|---|---|---|---|---|---|---|---|---|---|---|---|
| | | | | | | | | | I | $\eta$ FWHM | Area (%) | I | $\eta$ FWHM | Area (%) |
| Mosaicity is large when l is low | | | | | | | | | | | | | | |
| 6 | 12 | 2 | 7.9 | 1800 | 13.8 | 17.3 | 1 | 1 | 1814 | 6.2 | 56 | 1035 | 7.8 | 39 |
| −9 | −13 | 2 | 6.6 | 434 | 13.7 | 18.0 | 1 | 6 | 435 | 5.7 | 55 | 258 | 8.4 | 46 |
| 11 | 25 | 1 | 3.9 | 362 | 13.0 | 18.3 | 3 | 1 | 337 | 5.9 | 46 | 183 | 9.4 | 37 |
| 10 | 22 | 1 | 4.4 | 840 | 14.2 | 18.4 | 2 | 1 | 777 | 6.4 | 51 | 506 | 8.7 | 43 |
| 9 | 19 | 1 | 5.1 | 208 | 16.8 | 19.4 | 2 | 1 | 188 | 6.3 | 39 | 126 | 7.3 | 29 |
| 11 | 25 | −1 | 3.9 | 323 | 13.9 | 17.6 | 3 | 2 | 330 | 7.0 | 61 | 201 | 6.5 | 35 |
| 10 | 22 | −1 | 4.4 | 824 | 14.6 | 19.2 | 2 | 2 | 771 | 6.6 | 55 | 497 | 8.9 | 46 |
| 9 | 19 | −1 | 5.1 | 225 | 13.7 | 18.8 | 2 | 2 | 219 | 5.9 | 49 | 134 | 8.7 | 42 |
| 11 | 25 | −2 | 3.9 | 309 | 13.6 | 19.1 | 3 | 2 | 293 | 8.0 | 67 | 152 | 6.9 | 30 |
| 9 | 19 | −2 | 5.0 | 324 | 14.6 | 18.9 | 2 | 2 | 309 | 6.9 | 59 | 198 | 7.4 | 40 |
| −9 | −13 | −2 | 6.7 | 410 | 14.2 | 18.2 | 1 | 5 | 395 | 7.1 | 63 | 227 | 7.1 | 36 |
| Mosaicity is small when l is high and h and k are low | | | | | | | | | | | | | | |
| 1 | 5 | −42 | 4.2 | 805 | 2.8 | 4.4 | 2 | 3 | 494 | 2.1 | 52 | 306 | 4.2 | 45 |
| 1 | 3 | −31 | 5.8 | 408 | 2.3 | 4.0 | 2 | 3 | 264 | 2.2 | 60 | 169 | 2.0 | 37 |
| 0 | 6 | −53 | 3.3 | 541 | 2.9 | 4.4 | 3 | 3 | 363 | 2.2 | 54 | 210 | 2.2 | 31 |
| −1 | 5 | −56 | 3.2 | 505 | 2.5 | 3.6 | 3 | 3 | 415 | 1.5 | 65 | 216 | 0.3 | 24 |
| −2 | 4 | 40 | 4.4 | 185 | 4.9 | 6.3 | 2 | 0 | 131 | 1.6 | 43 | 121 | 3.5 | 57 |
| −3 | 5 | 48 | 3.7 | 435 | 4.2 | 6.3 | 3 | 0 | 329 | 0.8 | 38 | 259 | 4.1 | 56 |
| −3 | −3 | 17 | 9.7 | 1500 | 1.1 | 2.4 | 1 | 7 | 1286 | 0.3 | 58 | 663 | 0.5 | 32 |
| As l increases mosaicity decreases | | | | | | | | | | | | | | |
| −3 | −5 | −5 | 16.6 | 1412 | 15.8 | 19.1 | 0 | 5 | 1077 | 6.0 | 33 | 755 | 10.8 | 38 |
| −3 | −5 | −6 | 15.8 | 2035 | 14.1 | 18.3 | 0 | 5 | 1884 | 7.0 | 60 | 1005 | 8.0 | 36 |
| −3 | −5 | −7 | 14.9 | 1540 | 11.9 | 18.4 | 0 | 5 | 1491 | 6.1 | 58 | 809 | 8.1 | 40 |
| −3 | −5 | −8 | 14.3 | 880 | 12.0 | 17.2 | 0 | 5 | 829 | 6.3 | 62 | 455 | 7.0 | 37 |
| −3 | −5 | −9 | 13.6 | 666 | 11.1 | 16.7 | 0 | 5 | 619 | 5.8 | 55 | 350 | 7.3 | 37 |
| −3 | −5 | −10 | 13.0 | 893 | 11.5 | 15.6 | 0 | 5 | 811 | 5.9 | 59 | 465 | 7.3 | 39 |
| −3 | −5 | −11 | 12.3 | 3547 | 10.3 | 15.9 | 0 | 4 | 3353 | 5.9 | 62 | 1655 | 6.6 | 33 |
| −3 | −5 | −12 | 11.7 | 1194 | 11.3 | 16.1 | 0 | 4 | 998 | 5.3 | 49 | 658 | 8.3 | 45 |
| −3 | −5 | −13 | 11.2 | 638 | 10.0 | 14.1 | 1 | 4 | 604 | 5.6 | 64 | 299 | 6.7 | 36 |
| −3 | −5 | −14 | 10.5 | 841 | 10.3 | 15.6 | 1 | 4 | 696 | 5.0 | 48 | 441 | 8.1 | 43 |

Fig. 9 (Table 4)

| h | k | l | d (Å) | η total | η fit 1 | η fit 2 | Area (%) | |
|---|---|---|---|---|---|---|---|---|
| | | | | | | | Fit 1 | Fit 2 |
| −11 | −9 | 42 | 3.7 | 0.0034 | 0.0037 | −0.0022 | 93 | 0 |
| −12 | −6 | 55 | 3.0 | 0.0027 | 0.0025 | −0.0023 | 100 | 1 |
| 4 | 8 | −26 | 6.0 | 0.0050 | 0.0043 | −0.0021 | 77 | 1 |
| −12 | −10 | 43 | 3.5 | 0.0029 | 0.0029 | −0.0021 | 41 | 1 |
| 5 | 13 | −40 | 3.9 | 0.0043 | 0.0044 | 0.0029 | 92 | 1 |
| 9 | 23 | −37 | 3.2 | 0.0078 | 0.0073 | −0.0012 | 97 | 1 |
| 12 | 30 | 7 | 3.3 | 0.0134 | 0.0105 | 0.0024 | 35 | 3 |
| −15 | −15 | 36 | 3.5 | 0.0079 | 0.0068 | 0.0011 | 85 | 7 |
| −11 | −9 | 41 | 3.8 | 0.0020 | 0.0016 | 0.0016 | 41 | 7 |

Fig. 12 (Table 5)

| Diffraction Statistics | | | | | | | |
|---|---|---|---|---|---|---|---|
| Sample | Date | Orthogonal crystal dimensions (mm) | Crystal Volume. (mm$^3$) | Avg.† Max. Intensity (counts) | Avg.‡$_\eta$ (degrees) | No. Refl. | No. data frames |
| Earth-grown insulin crystals | | | | | | | |
| earth-1 | 12/98 | 0.35 X 0.35 X 0.32 | 0.04 | 344 | 0.031(0.017) | 170 | 2000 |
| earth-2 | 12/98 | 0.34 X 0.26 X 0.13 | 0.01 | 880 | 0.035(0.015) | 20 | 500 |
| earth-3 | 12/98 | 0.40 X 0.26 X 0.19 | 0.02 | 914 | 0.017(0.015) | 174 | 2000 |
| earth-4 | 7/99 | 0.43 X 0.34 X 0.19 | 0.03 | 81 | 0.038(0.024) | 14 | 2000 |
| earth-5 | 7/99 | 0.39 X 0.24 X 0.22 | 0.02 | 236 | 0.013(0.004) | 172 | 1999 |
| earth-6 | 7/99 | 0.39 X 0.24 X 0.17 | 0.02 | 172 | 0.023(0.010) | 72 | 2000 |
| Microgravity-grown insulin crystals | | | | | | | |
| μg-1 | 12/98 | 0.96 X 0.88 X 0.37 | 0.31 | 7510 | 0.004(0.002) | 502 | 2000 |
| μg-2 | 12/98 | 1.20 X 0.72 X 0.48 | 0.42 | 7811 | 0.006(0.005) | 241 | 1000 |
| μg-3 | 12/98 | 0.90 X 0.88 X 0.32 | 0.25 | 8195 | 0.004(0.004) | 176 | 500 |
| μg-4 | 7/99 | 1.29 X 0.84 X 0.43 | 0.47 | 12846 | 0.002(0.001) | 491 | 2000 |
| μg-5 | 7/99 | 1.72 X 1.31 X 0.90 | 2.04 | 8362 | 0.004(0.002) | 489 | 2000 |
| μg-6 | 7/99 | 1.59 X 1.59 X 0.50 | 1.25 | 7155 | 0.003(0.001) | 447 | 2000 |

*For the 12/98 data, $\Delta\lambda/\lambda=2.43 \times 10^{-4}$, vertical beam divergence $(\sigma_v)=19.5\ \mu$rad and horizontal beam divergence $(\sigma_\eta)=48.0\ \mu$rad. For the 7/99 data, $\Delta\lambda/\lambda=1.94 \times 10^{-4}$, $\sigma_v=15.5\ \mu$rad and $\sigma_\eta=43.6\ \mu$rad.

†The average peak height normalized for a 2 sec. exposure time is reported.

‡Standard deviation is given in parenthesis.

| Crystal | Dimer | Size(mm) | Course Collection | | Superfine Collection | | Cell Parameters a=b, c (Å) | Date Collected |
|---|---|---|---|---|---|---|---|---|
| | | | Time | Images | Time | Images | | |
| Microgravity | 0% | 1.12 x 0.96 x 0.72 | 20 sec | 20 | 2 sec | 2000 | 78.93, 38.02 | 7/99 |
| | 0.5% | 0.62 x 0.61 x 0.37 | 120 sec | 20 | 5 sec | 2000 | 78.51, 37.50 | 11/98 |
| | 0.9% | 0.40 x 0.26 x 0.19 | 60 sec | 20 | 5 sec | 1000 | 78.87, 37.87 | 11/98 |
| | 1.8% | 0.32 x 0.28 x 0.13 | 120 sec | 20 | 5 sec | 2000 | 79.09, 38.00 | 11/98 |
| | 3.6% | 0.54 x 0.37 x 0.26 | 60 sec | 20 | 5 sec | 2000 | 78.89, 38.06 | 11/98 |
| Ground | 0% | 0.86 x 0.40 x 0.40 | 20 sec | 20 | 2 sec | 2000 | 79.09, 38.09 | 7/99 |
| | 3.6% | 0.48 x 0.35 x 0.32 | 15 sec | 20 | 4 sec | 2000 | 78.87, 38.07 | 7/99 |

Fig. 15 (Table 6)

| Crystal | Dimer % | η average | Mosaicity (h,k,l) | | | Mosaicity(growth face) | | | $R^2$ | # ofRef. | No. Gauss | % reflections fitted by Gaussians | | | Average mosaicity, η | | |
|---|---|---|---|---|---|---|---|---|---|---|---|---|---|---|---|---|---|
| | | | $\eta_h$ | $\eta_k$ | $\eta_l$ | $\eta_{110}$ | $\eta_{101}$ | $\eta_{011}$ | | | | 1 | 2 | 3 | 1 | 2 | 3 |
| Earth | 0.0 | 8.4(3.3) | 4.1 | 8.3 | 14.4 | -0.1 | 5.1 | 9.3 | 0.12 | 857 | 2(1)+ | 27.8 | 72.2 | - | 4.0(1.7) | 5.4(1.8) | - |
| | 3.6 | 6.6(2.6) | 6.8 | 6.2 | 5.4 | 3.8 | 3.0 | 2.4 | 0.09 | 451 | 2 | 1.7 | 98.3 | - | 4.4(2.1) | 3.9(1.7) | - |
| Micro | 0.0 | 6.5(1.8) | 5.5 | 7.0 | 8.5 | 2.0 | 3.5 | 5.0 | 0.04 | 1499 | 2 | 13.1 | 85.6 | - | 5.3(1.2) | 3.9(1.6) | - |
| | 0.5 | 6.2(2.1) | 6.8 | 5.6 | 6.0 | 3.2 | 3.6 | 2.4 | 0.03 | 1305 | 2 | 1.4 | 93.7 | - | 4.9(10.9) | 4.0(4.7) | - |
| | 0.9 | 10.2(7.) | 8.2 | 10.8 | 15.6 | 1.7 | 6.5 | 9.1 | 0.04 | 931* | 2 | 29.0 | 71.0 | - | 9.9(7.4) | 9.5(6.7) | - |
| | 1.8 | 16.0(6.2) | 20.6 | 14.1 | 8.7 | 13.0 | 7.6 | 1.1 | 0.18 | 911 | 3 | 3.2 | 42.0 | 54.8 | 15.4(16.6) | 18.5(5.6) | 31.5(71.1) |
| | 3.6 | 7.4(1.7) | 8.5 | 7.5 | 3.2 | 6.4 | 2.1 | 1.1 | 0.12 | 1107 | 2 | 1.0 | 99.0 | - | 5.5(2.9) | 5.7(2.4) | |

Fig. 16 (Table 7)

METHOD FOR MEASUREMENT OF PHYSICAL CHARACTERISTICS OF CRYSTALS

TECHNICAL FIELD

The present invention generally relates to a method to measure the physical characteristics of crystals, and, in particular, to a method and apparatus which simultaneously measures the diffraction resolution and mosaic spread of macromolecular crystals.

BACKGROUND OF THE INVENTION

The use of reflective mosaicity has been used since 1981 (Shaikevitch et al., 1981) as an indicator of macro-molecular crystal perfection. Subsequently, synchrotron radiation was used to minimize the geometric and spectral contributions of the X-ray source to the experimental data (Colapietro et al., 1992; Helliwell, 1988). Mosaicity analysis of chicken egg-white lysozyme, apocrustacyanin $C_1$ and thaumatin crystals established a physical basis for the improvements seen in some microgravity-grown samples. In these samples, a reduction in the mosaic spread produced a corresponding increase in the signal-to-noise ratio of the reflection (Ng et al., 1997; Snell et al., 1995, 1997). The minimum mosaicities recorded were 0.005° for lysozyme, 0.030° for apocrustacyanin $C_1$, and 0.018° for thaumatin measured at the full-width at half-maximum (FWHM). These values were obtained by deconvoluting the spectral and geometric contributions of the X-ray beam from the recorded rocking width, which allowed a quantitative comparison between samples (Colapietro et al., 1992) independent of the instrument measuring them.

Successful measurement of mosaicity requires that the geometric and spectral parameters of the instrumentation do not mask the crystal characteristics. Synchrotron radiation is a useful tool for these studies, as it can provide a highly parallel and (when a suitable monochromator is used) a highly monochromatic beam (Helliwell, 1992; Margaritondo 1995). Specially configured in house x-ray sources could also be used.

Previous efforts have been devoted to reflections recorded individually with a scintillation counter mounted in the equatorial (vertical) plane by rotating the crystal about the horizontal axis which minimized the Lorentz effect and eliminated the contribution from the horizontal beam divergence of the synchrotron beam (Colapietro et al., 1992; Fourme et al., 1995; Helliwell, 1998; Ng et al. 1997; Snell et al., 1995). An algorithm and software for mosaic spread analysis using data from an area detector was developed in 1998 (Ferrer et al., 1998).

There is still a need for a method to accurately measure the physical characteristics of crystals where the measuring instrument itself does not mask the measurements being made.

There is a particular need for a method to simultaneously measure the diffraction resolution, mosaicity, and intensity data of macromolecular crystals.

SUMMARY OF INVENTION

The present invention addresses these needs. Typical measurements of macromolecular crystal mosaicity are dominated by the characteristics of the X-ray beam and, as a result, the mosaicity value given during data processing can be an artifact of the instrumentation rather than the sample. The present invention is an improved method for mosaic spread analysis which uses superfine Φ-slicing data collection, unfocused monochromatic radiation, and a suitable fast readout area detector, such as a charge-coupled device (CCD) X-ray area detector.

According to the invention, a fast readout area detector is used to rapidly record many reflections simultaneously. Suitable available protein crystallography software is used to assign indices which identify each reflection and to obtain standard crystallographic statistics, such as $I/\sigma(I)$ and diffraction resolution. Because the data are not all on the equatorial plane, horizontal divergence is a contributor to the recorded rocking width in addition to the vertical divergence and spectral spread contributions present in other methods. These effects are deconvoluted from the data so that the true crystal mosaicity is evaluated. The fast readout area detector makes the superfine Φ-slicing technique efficient and practical. The development of the crystal-quality evaluation method and the deconvolution of the beam divergence, spectral divergence and Lorentz effects from the measured rocking widths of the reflections are described herein. It is to be understood that the crystal rotations used in super fine Φ slicing can range from less than about 0.0001° to greater than about 1°, and that all such measurements are within the scope of the present invention. The processing is also described, along with examples of the technique using single crystals of manganese superoxide dismutase (MnSOD), insulin and lysozyme.

The present invention provides a method to physically characterize crystals by simultaneously measuring the diffraction resolution and mosaic spread of macromolecular crystals. The contributions of the X-ray beam to the reflection angular widths are minimized by using a highly parallel, highly monochromatic X-ray source. Many, tens to thousands, of reflection profiles over a wide resolution range are rapidly measured using an area detector (e.g. charge-coupled device (CCD)) in combination with superfine Φ-slice data collection. The Lorentz effect and beam contributions are evaluated and deconvoluted from the recorded data. For example, from 1° of superfine Φ-slice data collected on a crystal of manganese superoxide dismutase, the mosaicities of 260 reflections were measured. The average mosaicity was 0.0101° (s.d. 0.0035°) measured as the full-width at half-maximum (FWHM) and range from 0.0011 to 0.0188°. Each reflection profile was individually fitted with two Gaussian profiles, with the first Gaussian contributing 55% (s.d. 9%) and the second contributing 35% (s.d. 9%) of the reflection. On average, the deconvoluted width of the first Gaussian was 0.0054° (s.d. 0.0015°) and the second was 0.0061° (s.d. 0.0023°). The mosaicity of the crystal was anisotropic, with FWHM values of 0.0068, 0.0140° and 0.0046° along the a, b and c axes, respectively. The anisotropic mosaicity analysis indicates that the crystal is most perfect in the direction that corresponds to the favored growth direction of the crystal.

Methods according to this aspect of the present invention can be used, for example, to inspect a crystal's structure and its perfection. This method is of particular benefit in studying practical techniques of sample preparation for structural crystallography and for the use of crystals as a device rather than merely as a step to a structural solution.

In particular, the present invention relates to a method to simultaneously measure diffraction resolution and mosaic spread of a macromolecular crystal including the steps of (a) minimizing contributions of an x-ray beam to any reflection angular widths in the crystal by using a highly parallel, highly monochromatic x-ray source; (b) rapidly measuring multiple reflection profiles in the crystal over a wide resolution range using a suitable fast readout area detector in combination with superfine oscillation Φ-slicing imaging data collection; and (c) evaluating and deconvoluting the Lorenz effect and beam contributions from the recorded data.

In certain aspects, the method further includes the step of: (d) determining the direction in which the crystal is most imperfect.

In still further aspects, the method further includes the step of: (e) measuring accurate intensities through file slicing, deconvolution and profile fitting.

The superfine oscillating Φ slice data can be collected on a crystal where from about 0.0001° to about 1° of the super fine oscillation data is collected and where multiple reflection profiles are measured as the full-width at half-maximum (FWHM) or as the full width at quarter maximum (FWQM). Each reflection profile is fitted with at least one mathematical function that fits the recorded data. Preferably, the mathematical function is at least one Gaussian profile, is at least one Lorentzian profile, or other mathematical function.

Also the fast readout area detector is composed of a charge coupled device(s).

Mosaicity is determined from the measured reflection widths using formula $$\eta = \frac{|\varphi_R| - (L^2 \zeta^2 \gamma_v^2)^{\frac{1}{2}}}{(L/d)\cos\theta_{hkl}} \left(\frac{\delta\lambda}{\lambda}\right) \tan\theta_{hkl}.$$

In a preferred aspect, the diffraction data are processed by (a) indexing and integrating the 1° oscillation images using MOSFLM and scaling of data with suitable software to provide statistics on crystal quality, including the agreement between symmetry-related reflections Rsym and the signal-to-noise ratio I/σ(I); (b) using an orientation matrix to integrate the coarse oscillation image that corresponds with the superfine Φ-sliced images; (c) obtaining a reflection profile from the crystal by integrating the super fine Φ-sliced data; (d) removing random radiation events from the diffraction data; (e) locating the Φ position of the maximum value of the reflection; (f) calculating the width of the reflection as full width half-minimum (FWHM) and full-width at quarter-miminum (FWQM) and true crystal mosaicity η; and (g) fitting one or more mathematical functions that fit the data to all the reflection profiles.

In a preferred aspect, the accurate positioning of the maximum of the reflection allows for the increased accuracy in orientation matrix resulting in more accurate cell parameters.

Step (g) preferably comprises fitting the at least one mathematical function to the reflection profile wherein lmax/lbkg is greater than some arbitrary value (e.g. lmax/lbkg>1–10). The mathematical function preferably is at least one Guassian profile or at least one Lorentzian profile. Also a suitable signal-to-noise ratio can be used to filter out noise.

The reflection list includes indices for each reflection along with its detector coordinates for each reflection along with its detector coordinates for each reflection and the estimated error for each reflection. In a preferred aspect, 0.001° images are integrated at the reflection coordinate positions for reflections with a desired signal-to-noise ratio.

Further, in step (g) two Gaussian functions can be used. The initial Guassians are placed as follows before a fitting algorithm is employed. One Guassian function is placed at the maximum and the second Gaussian function is placed at the FWQM value to the right or left of the maximum by comparing the ratio of FWHM to FMQM for each side with that of a perfect Guassian.

The quality of the crystal is quantitatively analyzed by examining the reflection profiles recorded near a vertical equatorial axis. The relative contributions of domain misalignment and volume are distinguished from a variation of d spacing within a domain by analyzing mosaicity as a function of resolution. Then, angular separation between multiple peaks are used to measure misalignment of discrete domains. Thereafter, an anisotropic η calculation is applied to each individual mathematical function that were fit to the data profiles and then the measured mosaicity is used to identify types of imperfections existing with the crystal.

In another aspect, the present invention relates to a method for comparing different samples of crystals using symmetry related reflections obtained by using the methods described above.

In the methods described above, the Gaussian profile (s) is fit to the recorded data and deconvoluted using $$\eta = \frac{|\varphi_R| - (L^2 \zeta^2 \gamma_v^2)^{\frac{1}{2}}}{(L/d)\cos\theta_{hkl}} \left(\frac{\delta\lambda}{\lambda}\right) \tan\theta_{hkl}.$$

Further, a Fourier deconvolution can be used to remove inaccuracies in any broad reflection, and then the mathematical functions are fit to the data profile. The formula $F(\overline{\omega})=G(\overline{\omega})/I(\overline{\omega})$ can be applied where $F(\overline{\omega}), G(\overline{\omega})$, and $I(\overline{\omega})$ are the Fourier transforms of the true sample profile, the measured profile and the instrument function, respectively.

DESCRIPTION OF THE DRAWINGS

The claim of this patent contains at least one drawing executed in color.

FIG. 1(a) The (−5−3−51) reflection was broadened by Lorentz and beam effects and the measured FWHM value of $\Phi_R$ was 0.055°. Deconvolution resulted in a mosaicity of 0.007°.

FIG. 2(a) shows the corrections for beam characteristics and the Lorentz factor applied to the area-detector surface. This plot was generated by creating artificial data with a constant measured FWHM width of 0.020° on a two-dimensional grid across the detector face and then applying the deconvolution equation to each point. Values for the resulting mosaicity (η) value are in thousandths of a degree. In the vertical region small corrections (0.002) were applied, giving an η value of 0.018°; the correction increased radially towards the horizontal region (dark area). FIG. 2(b) shows the definition of detector sections and resolution rings. The upper resolution limit was 11.7, 5.9, 4.0 and 3.0 Å for rings 0, 1, 2 and 3, respectively. The Φ rotation axis is horizontal in both parts.

FIG. 3a(a) FWHM $\Phi_R$ and FIG. 3(b) the corresponding η. For clarity, the detector dimensions are elongated along the x axis. A dashed line indicates the horizontal rotation axis. Pixel size was 0.1632 mm. Symbols are color coded to indicate FWHM values (in thousandths of a degree) and are grouped into three ranges. In the symbol legend above the plots, values between 0 and 5.9 are white, between 6 and 3.9 are grey and between 14 and 20 are black. Symbols within each group are ranked circle<diamond<triangle<square.

FIG. 4 is Table 1 which shows reciprocal space, mosaicity and relative mosaic block size statistics.

FIGS. 6 and 7, are Tables 2 and 3, respectively, which demonstrate anisotropy of mosaicity (e.g. mosaicity is large when l is low and vice versa).

FIG. 9 is Table 4 which shows that for 20 reflections the smaller second Gaussian is only 10–25% of the total reflection. FIG. 9 (Table 4) shows that for all but one of the single-Gaussian reflections l is much larger than h or k, which is consistent with the low calculated mosaicity along the l direction and confirms the anisotropic η calculation for this crystal.

FIG. 11(a) microgravity grown and FIG. 11(b) earth grown.

FIG. 12 is a Table 5 showing diffraction statistics for earth grown insulin crystals and microgravity-grown insulin crystals.

FIG. 15 is Table 6 which shows experimental data collection parameters and crystal sizes for lysozyme crystals grown in microgravity and on earth and doped with varying percent impurity. The size was evaluated by measuring the largest dimension then the other two perpendicular dimensions. For each crystal two 10° swaths of coarse data with ΔΦ=1° were collected 90° apart. Two 1° swaths of superfine Φ sliced data as 0.001° separated stills were then collected. For the ground 3.6% case swathes were collected 45° apart. The space group for all crystals was $P4_32_12$.

FIG. 16 is Table 7 which shows the anisotropic refinement of mosaicities for lysozyme crystals. $R^2$ is the goodness of fit of the anisotropic mosaicity. The number of Gaussians fitted to the data is also noted with the % of reflections fitted. For the 0% dimer earth sample the two swaths of data collected were fitted to one and two Gaussians, respectively. The average mosaicity for each Gaussian is noted with the standard deviation in brackets, both in thousandths of a degree. Due to differences in exposure times (Table 5) it is inappropriate to compare the number of reflections between crystals. *Note, only 1° of data was collected for the 0.9% superfine sliced data in comparison with 2° for the rest of the data.

DETAILED DESCRIPTION OF THE PREFERRED EMBODIMENT

Figure 1A:
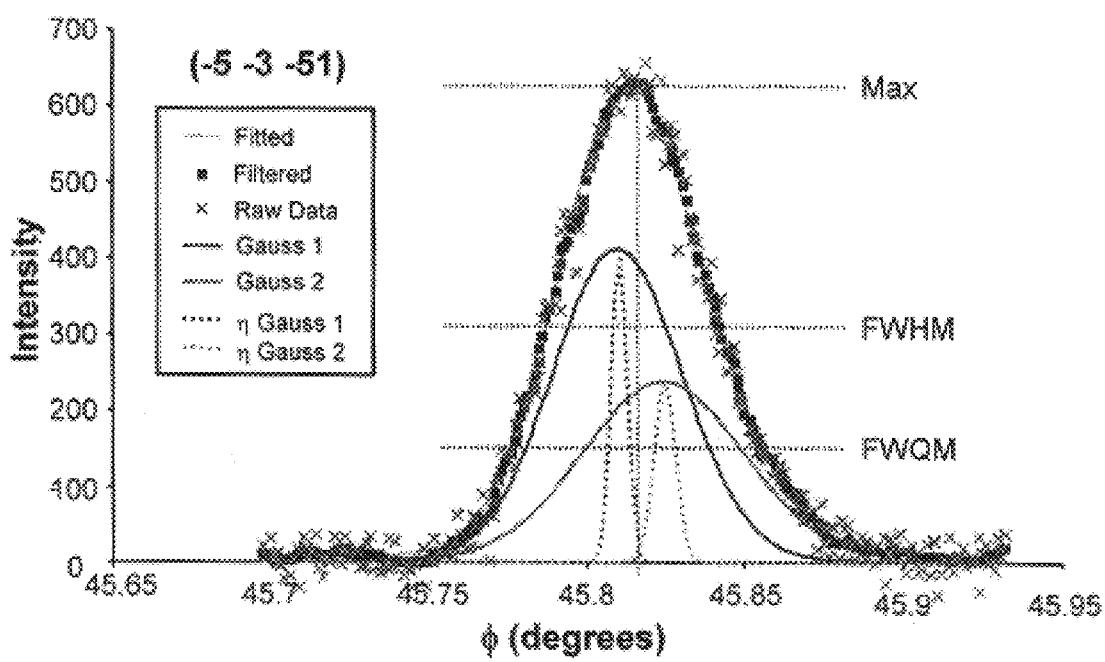
FIGS. 1a and b are graphs showing examples of reflection profiles and Gaussian fits.

The mosaic nature of crystals was proposed by Darwin (1922) and approximates the crystal to a series of perfectly ordered volumes (domains) slightly misaligned with respect to each other. The reflection profile is broadened by the misalignment between domains, the volume of the domains (from Fourier truncation), and any lattice variation between them (Boggen et al., 2000; Nave, 1998). Therefore, mosaicity is a measure of the long-range order within the crystal.

The width of the reflection profile is also broadened by the geometric and spectral parameters of the X-ray source used (Greenbough et al., 1982). The vertical and horizontal crossfire angles at the same, $\gamma_v$ and $\gamma_h$, respectively, together with the wavelength dispersion δλ/λ contribute to the reflection broadening. Additionally, differences in the motion of reciprocal-lattice points through the Ewald sphere broaden reflections by varying amounts. The Lorentz correction (L) compensates for this effect. The angular width, $\Phi_R$, for a reflection in the case of a horizontal rotation axis and a Gaussian profile is given by formula (1) below, adapted from Helliwell J. R., Macromoledular Crystallography with Synchrotron Radiation, Cambridge University Press (1992).

$$|\varphi_R| = (L^2 \zeta^2 \gamma_v^2)^{\frac{1}{2}} + \frac{L}{d}\cos\theta_{hkl}\left[\eta + \left(\frac{\delta\lambda}{\lambda}\right)\tan\theta_{hkl}\right].$$

Here, η is the mosaic spread, ζ is the position of the corresponding reciprocal-lattice point projected onto the rotation axis and d is the resolution (d=λ/2 sin $\theta_{hkl}$). In Formula (1), the correlated dispersion (i.e., the wavelength variations across the beam) is ignored. In h and v are the horizontal (along the rotation axis) and vertical distance of the observed reflection from the direct-beam position, respectively, then ζ is given by Formula (2)

$$\zeta^2 = \left(\frac{h^2}{h^2 - v^2}\right)\sin^2(2\theta_{hkl}).$$

The Lorentz correction is given by Formula (3)

$$L = \frac{1}{[\sin^2(2\theta_{hkl}) - \zeta^2]^{\frac{1}{2}}}.$$

The reflection angle $2\theta_{hkl}$ is given by Formula (4)

$$2\theta_{hkl} = \tan^{-1}\left[\frac{(h^2 + v^2)^{\frac{1}{2}}}{XTD}\right],$$

where XTD is the crystal-to-detector distance.

It can be seen in Formula (1) that $\gamma_v$ broadens the reflections universally over the detector, whereas $\gamma_h$ broadens the reflection profile by an amount that depends on the position of the reflection. The Lorentz effect is maximal along the rotation axis, which is horizontal in the present case. The wavelength-dispersion term has its largest effect on high-resolution reflections. To evaluate the mosaicity of the crystal sample accurately, the crossfire angles and wavelength-dispersion terms need to be as small as possible. A properly configured synchrotron beamline delivers a very parallel intense X-ray beam with little wavelength dispersion. Mosaicity is calculated from the measured reflection widths by rearranging Formula (1), as shown in Formula (5) below.

$$\eta = \frac{|\varphi_R| - (L^2\zeta^2\gamma_h^2 + \gamma_v^2)^{\frac{1}{2}}}{(L/d)\cos\theta_{hkl}} - \left(\frac{\delta\lambda}{\lambda}\right)\tan\theta_{hkl}.$$

EXAMPLE I

The first step in data processing is the determination of the unit-cell parameters and the orientation matrix using suitable processing suites such as MOSFLM.

The unit-cell parameters were a=100 Å, b=108.3 Å, c=180.7 Å. The data from the four 1.0° images are only 9.6% complete and do not contain enough reflections to provide reliable statistics for assessment of crystal quality. By collecting more 1.0° images, reliable $1_{sym}$ and $1/\sigma(1)$ versus resolution statistics about the crystal are obtainable. The diffraction limit of the MnSOD crystal, defined to be the resolution with $1/\sigma(1)$ dipped below 2.0 in this relatively weak unfocussed synchrotron beam, is 3.0 Å. In comparison, data collected at the more intense SSRL beamline 7-1 operating in focused mode from the cryocooled piece of this crystal yield 1.3 Å resolution.

Figure 1B:
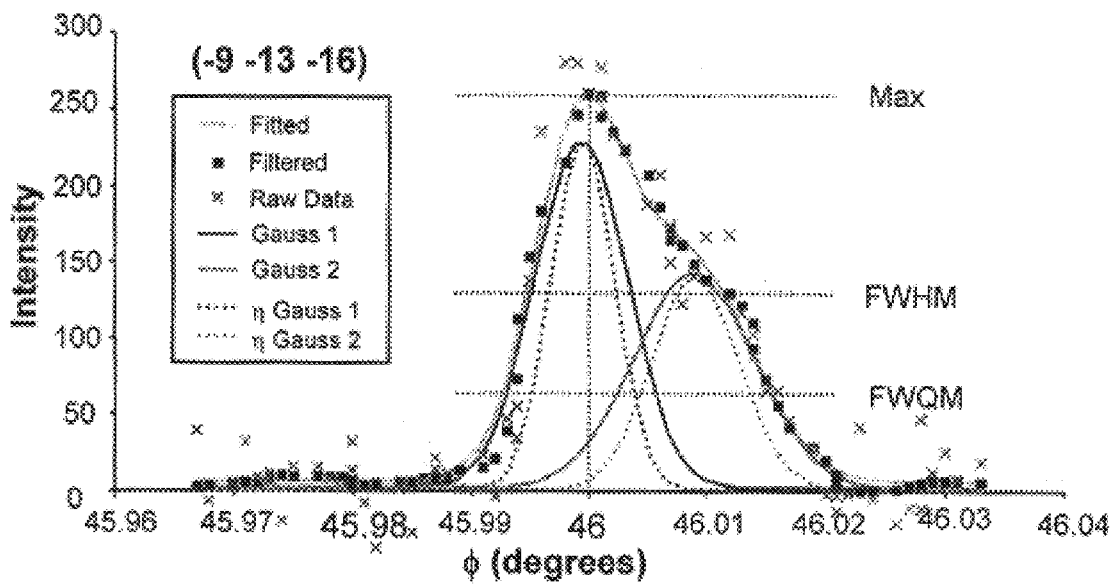
FIG. 1(b) The (−9 −13 −16) reflection lies along the vertical axis. The measured FWHM value was 0.0173° and the deconvoluted FWHM mosaicity was 0.0130°. Definitions for FWHM and FWQM are indicated. The positions of these reflections on the detector are indicated with arrows in FIG. 3.
Figure 2A:
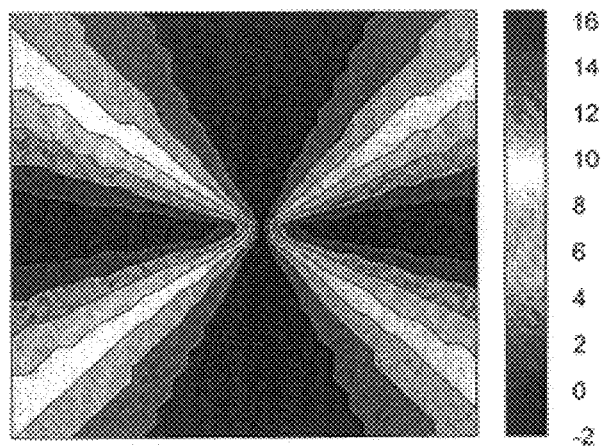
FIGS. 2a and 2b show the analyses of corrections applied and definition of detector sections and rings.
Figure 2B:
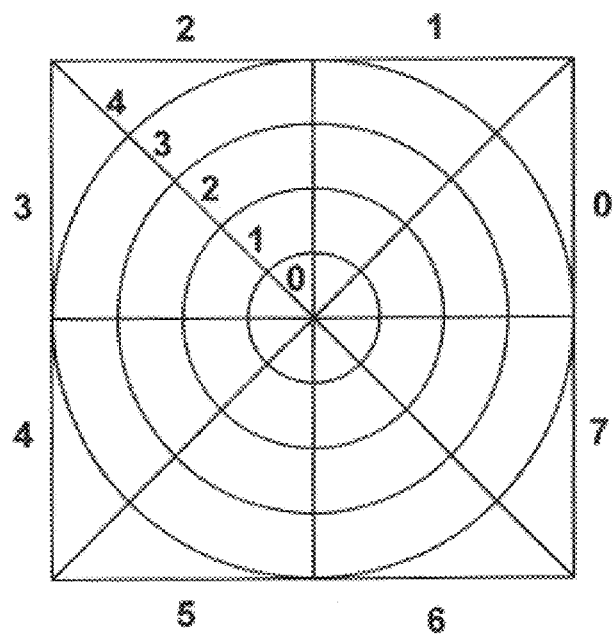
Figure 3:
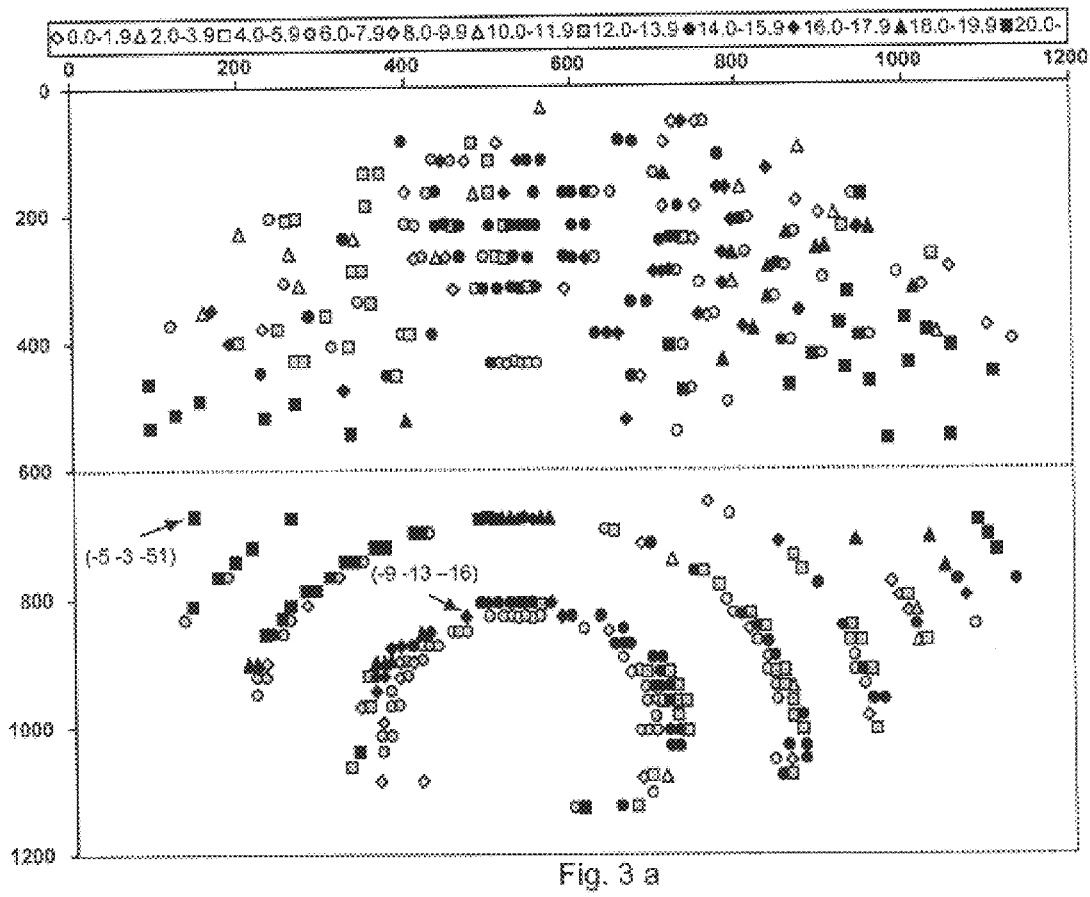
FIGS. 3a and 3b are graphs showing measured reflection-profile widths and mosaicity plotted on the detector face (in pixels).
Figure 3:
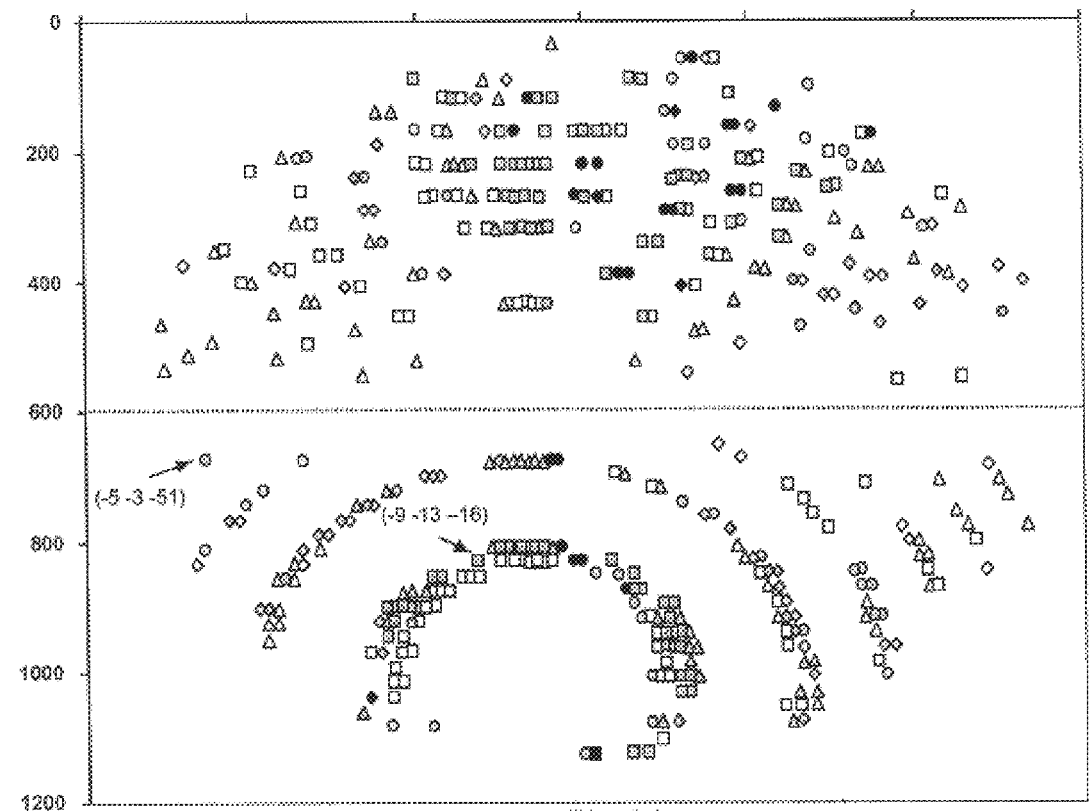

The quality of the protein crystal is quantitatively evaluated by examining the reflection profiles as seen in FIG. 1. Reflection profiles along the horizontal rotation axis (FIG. 1a) are dramatically broadened by the beam and Lorentz effects. On the other hand, the reflections recorded near the vertical equatorial axis (FIG. 1b) are minimally broadened and their observed widths are closed to the true crystal mosaicity. For this experiment, the deconvolution equation (5) reduces the measured $\Phi_R$ FWHM values minimally near the vertical axis and the correction increases towards the horizontal axis, as seen in FIG. 2a. When the FWHM values of $\Phi_R$ for 1° of fine $\Phi$-slicing data are plotted according to their position on the CCD detector, the instrumental broadening along the horizontal can be seen (FIG. 3a). The deconvolution of $\Phi_R$ to $\eta$ effectively removes the instrumental broadening (FIG. 3b). The values of $\eta$ across the detector face are not homogeneous (FIG. 3b).

From 1° of superfine $\Phi$-sliced data, the mosaicities of 260 reflections are analyzed as shown in FIG. 4, Table 1 below. The FWHM mosaicity values ranged from 0.0011 to 0.0188°, with an overall average of 0.0101° (s.d. 0.0036°).

FIG. 4 (Table 1) which shows reciprocal space, mosaicity and relative mosaic block size statistics. Sector average values for mosaicity, $\eta$, in thousandths of degrees are followed by the standard deviation in parentheses. The five reflections that fit with negative values for the second Gaussian were omitted from the Gaussian statistics. The percentage of the total peak area arising from the constant background is not reported.

Figure 5:
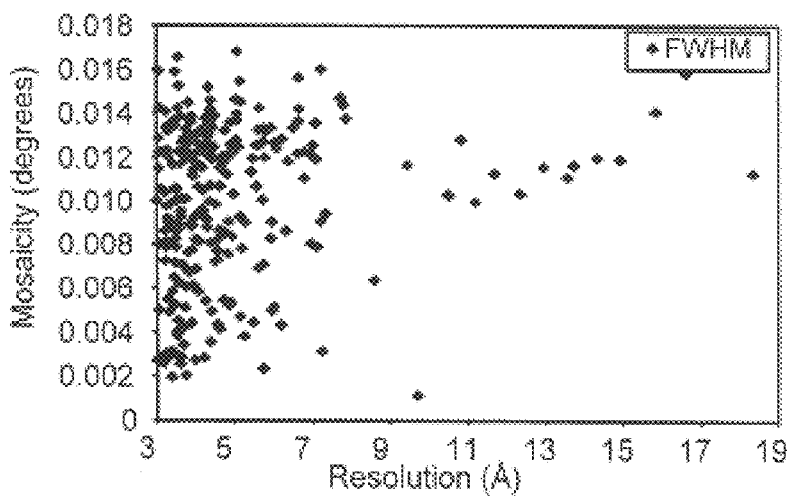
FIGS. 5a, b and c are plots of mosaicity against resolution for all data for FIG. 5(a) FWHM, FIG. 5(b) FWQM and FIG. 5(c) each Gaussian.
Figure 5:
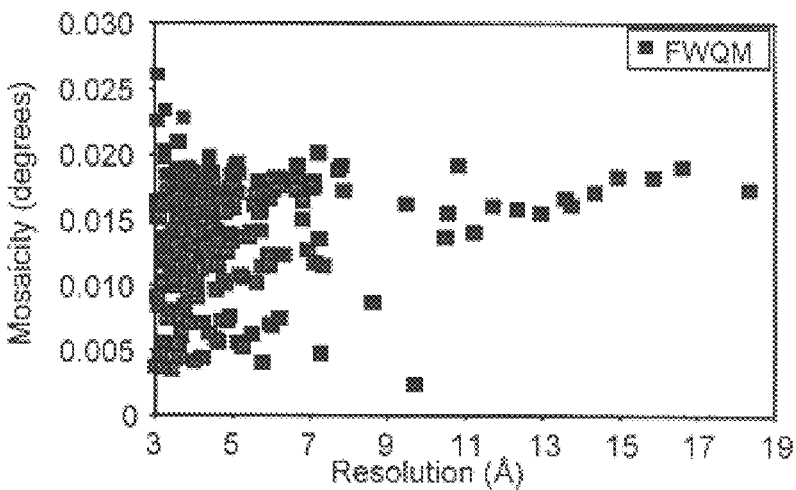

A large range of values is seen in the FWHM mosaicity. For asymmetric reflections with a shoulder on one side, the FWHM calculation could underestimate the width of the reflection, whereas the FWQM would be more likely to include the full width (FIG. 1). The FWQM mosaicity values ranged from 0.0024 to 0.0261°, with an average of 0.0138° (s.d. 0.0045°; FIG. 4 Table 1). For the FWQM measurements both the average peak width and the standard deviation increased by about 1.3-fold, indicating no reduction in the scatter in the data. Therefore, underestimating the reflection width does not account for the large range of the mosaicity data (FIGS. 5a and 5b). The large range is in fact an indicator of anisotropic mosaicity as is shown below.

Figure 5C:
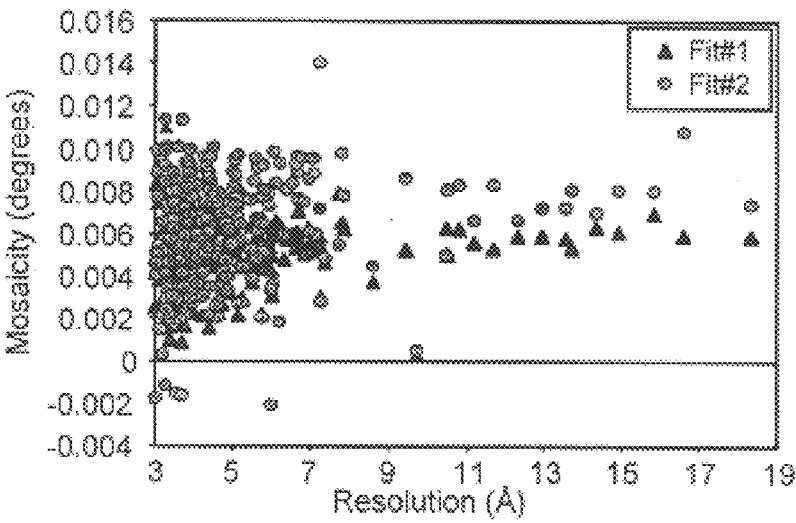

The majority of the reflection profiles had a shoulder peak to the right of the main peak (FIG. 1b). Therefore, all reflection profiles were automatically fitted with two Gaussian profiles. A Gaussian profile approximates the instrument incident radiation profile. The primary Gaussian contributed 55% (s.d. 9%) and the secondary Gaussian contributed 35% (s.d. 9%) of the reflection. On average, the deconvoluted width of the first Gaussian was 0.0054° (s.d. 0.0015°) and the second was 0.0061° (s.d. 0.0023°). Overall, the majority of the data were fitted well with two Gaussians. Five reflections gave a negative deconvoluted width for the second Gaussian (FIG. 5c), indicating that they could have been better fitted with a single Gaussian. FIG. 4 (Table 1) shows that the fraction of the reflection intensity attributed to each Gaussian remains relatively constant throughout the data set. This indicates that the two Gaussian model is well matched to this data set.

The data in FIG. 4 (Table 1) also show that the symmetry-related sections (e.g. 0 and 4) have very similar mosaicity values (see also FIG. 3b). The internal consistency of the data is also shown by the results for the symmetry-related reflections in FIG. 6 (Table 2).

FIG. 4 (Table 1) also shows that although the mosaicity varies considerably between the sectors, within each sector the mosaicity does not vary greatly with resolution. The observed dependence of mosaicity on direction but not resolution is to be expected from a crystal exhibiting anisotropic mosaicity, whereas errors in the deconvolution formula or the beam parameters would be expected to produce resolution-dependent effects.

The relative contributions of domain misalignment and volume can be distinguished from the variation of d spacing within a domain by studying mosaicity as a function of resolution. Domain-misalignment and volume effects are independent of resolution, whereas mosaicity arising from variation of d spacing is dependent on resolution. For isotropic mosaicity, this is a simple test; however, the MnSOD data shows significant anisotropy. The plot of mosaicity versus resolution (FIG. 5) indicates that the mosaicity is fairly constant at low resolution and variable at higher resolution. The increase in variability with resolution is probably a consequence of the anisotropic mosaicity.

The anisotropic nature of crystal mosaicity was illustrated by Snell et al., Acta Cryst. D53, 231–239 (1997) as a three-dimensional vector plot. The individual reflection's mosaicity was the vector magnitude and the indices were the direction. Ferrer et al., J.Appl. Cryst. 31, 523–532 (1998) later introduced a mathematical formula of this given by (6)

$$\eta_{hkl}^{calc} = \frac{\eta_h h^2 + \eta_k k^2 + \eta_l l^2}{h^2 + k^2 + l^2}.$$

Here, $\eta_h$, $\eta_k$ and $\eta_l$ represent the anisotropic components of mosaicity. With this model, $\eta_h$, $\eta_k$ and $\eta_l$ were calculated using a matrix representation of multivariate regression analysis of all 260 measured mosaicity values. For the MnSOD crystals, FWHM values of $\eta_h$, $\eta_k$ and $\eta_l$ were 0.0068, 0.0140 and 0.0046°, respectively. Inspection of the mosaicity values and their indices (FIGS. 6 and 7, Tables 2 and 3) shows the mosaicity is large when l is low and vice versa. In addition, when a group of reflections with constant values of h and k was studied it was seen that as l increases mosaicity decreases.

Figure 8:
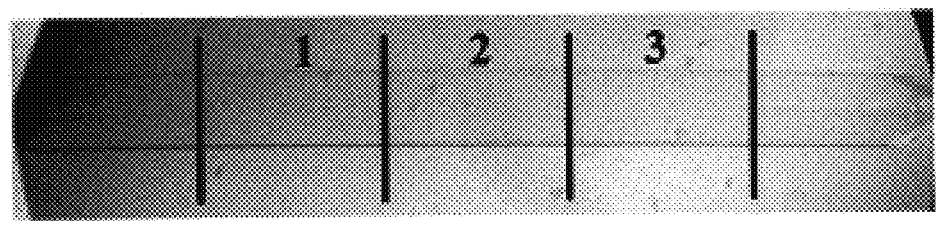
FIG. 8 is a photograph of a long single crystal of E. coli MnSOD grown from 50 mM Bicine pH 8.5 and 25% PEG 6000. This crystal is square in cross section (120×120 μM), over 1 mm long and was cut into several pieces each approximately 250 μM long along the lines indicated. Pieces 2 and 3 were cryocooled and diffraction data were collected at SSRL beamline 7-1 for structure determination. The structure was determined using data from piece 3. Piece 1 was mounted in a capillary and room-temperature crystal mosaicity measurements were taken at SSRL beamline 1-5 in unfocussed mode using superfine Φ-slicing the following day.

In a very narrow set of data, the range of h indices is less than that for k and l and therefore information on the crystal properties along the h direction is less certain than in the other two directions. The data indicate that the crystal is most perfectly ordered along the c direction. The c direction contains a twofold screw axis, corresponds to the longest unit-cell dimension and lies along the length of the needle-shaped crystal (FIG. 8). The direction of highest perfection therefore lies along the direction of favored growth. The reduction of mosaicity in this direction is similar to that seen for another needle-shaped crystal, apocrustacyanin $C_1$ described in Snell et al., (1997).

It has been suggested by Shaikevitch, et al. (1981) that lattice errors, local or extended, cause dislocations and therefore a tilt angle between mosaic domains. These lattice errors can propagate by two methods: accumulation of systematic errors or a random statistical distribution. Systematic errors will be linearly proportional to the number of unit cells, whereas random errors are proportional to the square root of the number of cells. The MnSOD mosaicity data indicates that systematic rather than random errors exist in the MnSOD crystal. Combining Shaikevitch et al. (1981) systematic error model and the calculated anisotropic mosaicity values ($\eta_h$=0.0068, $\eta_k$=0.0140, $\eta_l$=0.0046°) gives an average mosaic block with dimensions 83, 44 and 223 µm along h, k and l, respectively. The crystal is approximately 250 µm long in the c direction or about the calculated domain size (FIG. 8). In the other directions, two or more blocks could fit within the dimensions of the crystal. The alternative random-error model gives a mosaic block size that encompasses the entire crystal in all three dimensions. In the analysis of the MnSOD crystal, all of the reflections were automatically fitted with two Gaussians and for the large majority of the reflections the two Gaussians assumed a fairly constant percentage ratio of 55:35 on average. However, nine reflections were primarily composed of one Gaussian (FIG. 9, Table 4) and for 20 reflections the smaller second Gaussian is only 10–25% of the total reflection. FIG. 9 (Table 4) shows that for all but one of the single-Gaussian reflections l is much larger than h or k, which is consistent with the low calculated mosaicity along the l direction. These results support the systematic error model and not the random-error model that predicts a crystal of this size to be a single domain.

This MnSOD crystal was a challenging sample to evaluate owing to its large unit cell and asymmetric reflection profiles. There was a large variation in mosaicity over the range of reflections examined. Using the fine-slicing method with synchrotron radiation and a fast-readout CCD detector, crystal mosaicity was evaluated using 260 reflections from 1° of data. The reflections were recorded simultaneously at different resolutions and indexed to facilitate sample comparison. The same experimental setup allows the collection of conventional rotation data so that the conventional crystallographic parameters $R_{sym}$ and $1/\sigma(I)$ can be used in the comparison. The ability to record a large amount of mosaicity data rapidly from a single sample allows a more robust statistical analysis of crystal quality than had previously been achieved.

Three types of crystal imperfections contribute to increased mosaicity: domain misalignment, domain volume and defect or impurity incorporation (Boggon et al., 2000; Nave, 1999). The measured mosaicity contains information that can be used to identify the type of imperfections existing within a crystal sample. Volume and misalignment effects are independent of resolution and it is not possible to distinguish between the two with mosaicity analysis alone. Variation of d spacing owing to defect or impurity incorporation is dependent on resolution, but no clear resolution trends exist in the MnSOD data.

Two additional pieces of information are contained in the data once it has been fitted with two or more Gaussian peaks. Firstly, the angular separation between multiple peaks can measure the misalignment of discrete domains. Secondly, the anisotropic η calculation could be applied to each Gaussian peak. It is not appropriate to apply either of these analyses to the MnSOD sample owing to the limited area of reciprocal space collected. The collection of at least two orthogonal swaths of the superfine Φ-sliced data is necessary for this form of analysis. The approximation of the reflection profile to the sum of two Gaussians appears to be reasonable as shown by the large (approximately 90%) and relatively constant fraction of the intensity accounted for by the two Gaussians, while a more theoretically rigorous and computationally intensive method would be a Fourier deconvolution of the true crystal mosaicity (Snell, 1998). This was not necessary for the analysis of the MnSOD crystal, but for crystals with reflection profiles composed of many components the Fourier method may be desired.

The following data provides the detailed analysis of the information described above:

Crystal Sample—MnSOD from *Escherichia coli* was purified and crystallized as described in Borgstahl et al., J.Mol.Biol. 296, 951–959 (2000). The space group was $C222_1$, with unit-cell parameters a=99.1, b=107.3, c=179.1 A. The asymmetric unit was composed of two MnSOD homodimers. A long single crystal was cut into several pieces (FIG. 8). High-resolution cryocooled diffraction data were collected from one of the pieces at Stanford Synchrotron Radiation Laboratory (SSRL) beamline 7-1. The crystal diffracted to 13 A resolution, but in order to obtain adequate reflection separation it was necessary to collect data at a distance that only allowed 1.55 A data to be recorded. Data were 100% complete with $R_{sym}(I)$=7.0% overall and $R_{sym}(I)$=24.1% in the highest resolution shell (1.55–1.64 A). Data redundancy was 1.7-fold overall. Refinement and structural results were reported in Borgstahl et al., (2000). Data reduction with MOSFLM (Leslie, (1990), Leslier, (1999); Steller et al., (1997); Powell, (1999)) measured the crystal mosaicity to be 0.7°. It should be noted that this average mosaicity includes contributions from the focused synchrotron beam (≈0.3%) plus the true crystal mosaicity (increased by cryocooling).

Fine-Slicing Data Collection—For mosaicity analysis, another piece of the MnSOD crystal was mounted in a sealed 0.7 mm glass capillary with the long axis of the crystal along the capillary axis. Slugs of mother liquor were placed at both ends of the capillary. No visible crystal defects were noted.

Data were collected at SSRL beamline 1–5 operating in unfocused mode. The FWHM of the vertical and horizontal divergences of the beam were calculated to be 19.5 and 48 $\mu$rad, respectively. The wavelength was calibrated by measuring the X-ray absorption edge of a metal foil. All data were collected at a wavelength of 1.000 A. The wavelength dispersion from the double-crystal Si(111) monochromator was calculated to be $2.43 \times 10^{-4}$. The correlated dispersion of the beam at the sample position was calculated to be $2.5 \times 10^{-4}$ A mm$^{-1}$ in the vertical direction. There is no horizontal dispersion. Since the sample crystal as mounted was only 0.2 mm in the vertical direction, the difference is average wavelength over the extent of the crystal was $5.0 \times 10^{-5}$ A. This value is small enough relative to the wavelength dispersion from the monochromator to justify dropping the term for correlated dispersion from Formula (1), particularly for the relatively low resolution limit of the data in this example. An ADSC Quantum 4 CCD detector was used to collect the data. The detector was operated in 2×2 binned mode for faster readout. To save time during data collection, dezingering (i.e. taking two identical exposures and removing differences to compensate for the detection of random environmental radiation) was not used.

Figure 10:
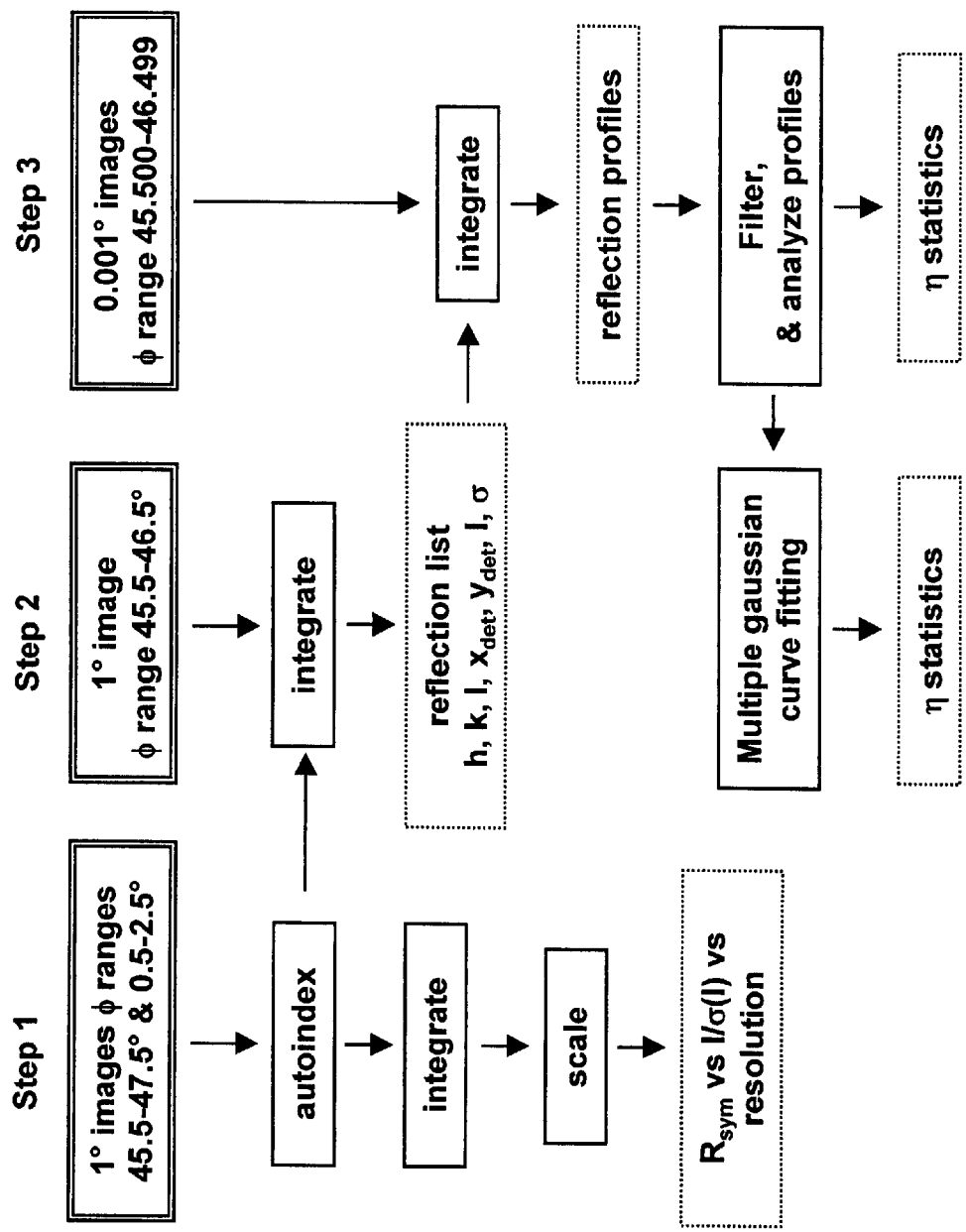
FIG. 10 is a flow diagram of the three steps involved in processing the MnSOD diffraction data. MOSFLM, an available structural protein crystallography software, was used in steps 1 and 2 for autoindexing and integration. Integration in step 3 was performed with software provided by ADSC Inc. Software written by the inventors was used for all other parts of step 3. The overall data processing was managed by a graphical user interface called BEAM-ish.

Crystal temperature was maintained at 295±0.1 K using an FTS air-stream system. The crystal-to-detector distance was 260 mm. For crystal orientation, unit-cell parameter determination, indexing and assessment of diffraction resolution, 1° oscillations of 60 s duration were collected over two 2.0° $\Phi$ ranges separated by 45° (FIG. 10). For mosaicity analysis, still images separated by 0.001° of 5 s duration were then collected over a 1° $\Phi$ range (83 min$^{-1}$). The optimum range for superfine data collection was selected by examining the 1.0° images. Reduction gearing enabled the $\Phi$ axis to move in steps as small as 0.0005°.

Data Processing—The MnSOD diffraction data were processed in three steps (FIG. 10). In the first step, the 1° oscillation images are auto-indexed and integrated using MOSFLM and then scaled together with SCALA using smooth scaling (Collaborative Computational Product, Number 4, 1994; Evans, (1997); Kabsch, (1988); Leslie, (1999); Powell, (1999)). This step provides statistics on crystal quality, including the agreement between symmetry-related reflections $R_{sym}$ and the signal-to-noise ratio $1/\sigma(I)$. The orientation matrix is then used in the second step to integrate the 1° oscillation image that corresponds with the superfine $\upsilon$-sliced images. MOSFLM outputs a reflection list (called the mtz file) that includes the indices for each reflection along with its detector coordinates and estimated error. By default, MOSFLM omits reflections from this reflection list with widths greater than 5° owing to the Lorentz effect. Such reflections were therefore not used in the following mosaicity analysis.

In the third step, the mosaicity data from the crystal was obtained by integrating the superfine $\Phi$-sliced data with software provided by ADSC. All the 0.001° images were integrated at the MOSFLM-predicted reflection coordinate positions for reflections with $1/\sigma(I)>3.5$; the output contained integrated intensities for each reflection for each image. Random radiation event in the phosphor or optical taper (known as "zingers") were then removed from the diffraction data, reflection profiles were located and the reflection width and the true crystal mosaicity η were calculated. Zingers were identified as extremely large intensities that existed on only one image. The zingers were erased and replaced with the average intensity of the neighboring images. To remove noise from the data, a three-point moving average filter was applied. The $\Phi$ position of the maximum value of the reflection was then located and the width of the reflections was calculated as FWHM and full-width at quarter-maximum (FWQM) values (FIG. 1).

Multiple Gaussian functions were automatically fitted to all the reflection provides with $1/\sigma(I)>5.0$ using MATLAB subroutines. For each reflection, a range of data that was three times the FWQM value about the reflection maximum was used. Two Gaussians fit the reflection profiles optimally. Use of three Gaussians did not significantly reduce the residual. The automatic curve-fitting routine initially placed one Gaussian at the maximum and one at the FWQM value to the right or left of the maximum. The proper side for the second Gaussian was determined by comparing the ratio of FWHM to FWQM for each side with that of a perfect Gaussian. The Levenburg-Marquett algorithm was then used to perform a non-linear least-squares fit on the data. A constant background was applied and constrained to be greater than zero. No user intervention was required for this step.

EXAMPLE II

Diffraction data from rhombohedral crystals of hexameric insulin complexed with zinc in a 6:2 ratio were first recorded in 1925 and the first structures of pig insulin determined 45 years later at 2.8 and 2.5 Å resolution using sealed-tube X-ray sources (Baker et al., 1988 and references therein). To date, the highest resolution structure reported from earth-grown rhombohedral human insulin crystals is at 1.5 Å (Protein Data Bank entry 4INS and Ciszak et al., 1994) obtained with a rotating-anode X-ray source. The $T_6$ form of rhombohedral human insulin crystals was grown in microgravity during the STS-95 Space Shuttle Mission and data beyond 0.9 Å have been collected from cryocooled crystals at a synchrotron (Smith, G. D., personal communication). Microgravity growth is thought to increase the physical perfection and volume of crystals by the reduction of buoyancy, convection and sedimentation effects (Pusey et al., 1988, Pusey et al., 1986) and early evidence had shown that growth in microgravity fostered improved order in protein crystals (Snell et al., 1995, Ng et al., 1997). Therefore, the physical characteristics of microgravity and earth-grown insulin crystals were measured in order to explore the reasons why growth in a microgravity environment improved their X-ray diffraction quality.

Materials and Methods

Crystal Growth: Crystals were grown in Commercial Protein Crystallization Facility (PCF) (Long et al., 1996) during the nine day STS-95 Space Shuttle Mission starting Oct. 29, 1998. Crystals were grown by the batch method and nucleation in microgravity was controlled by temperature as described previously by Long et al. (1996). This method of growth eliminates the deleterious effects of Marangoni convection seen when vapor diffusion methods are used in microgravity (Chayen et al., 1997). The Earth crystals were grown with identical biochemical conditions at the same time in a duplicate of the PCF apparatus. Prior to data collection, the crystals remained in their unopened PCF bottles at 22° C.

Data Collection: In order to minimize instrumental smearing effects, highly-parallel and highly-monochromatic synchrotron radiation was used at the Stanford Synchrotron Radiation Laboratory (SSRL) bending-magnet beamline 1–5. To provide a statistically valid number of measurements in a reasonable amount of beamtime, data were collected with a Quantum-4 CCD detector (ADSC) using the rotation camera geometry.

Figure 11:
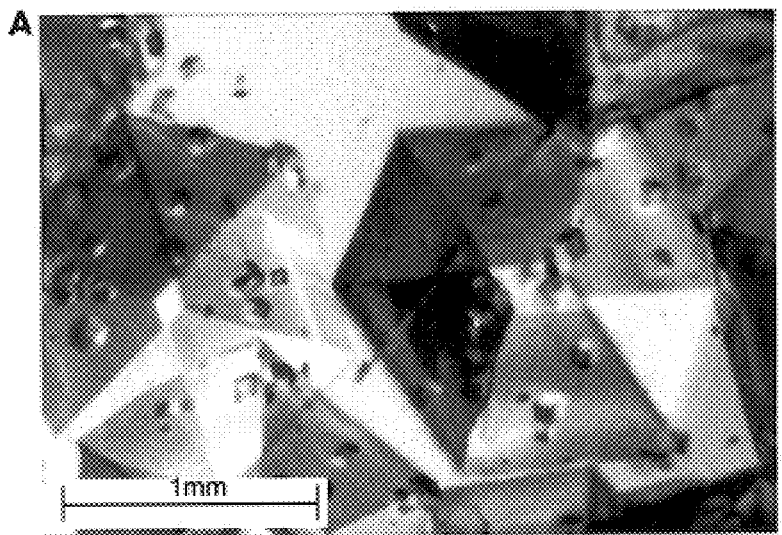
FIGS. 11a and b are photographs of representative insulin crystals.
Figure 11:
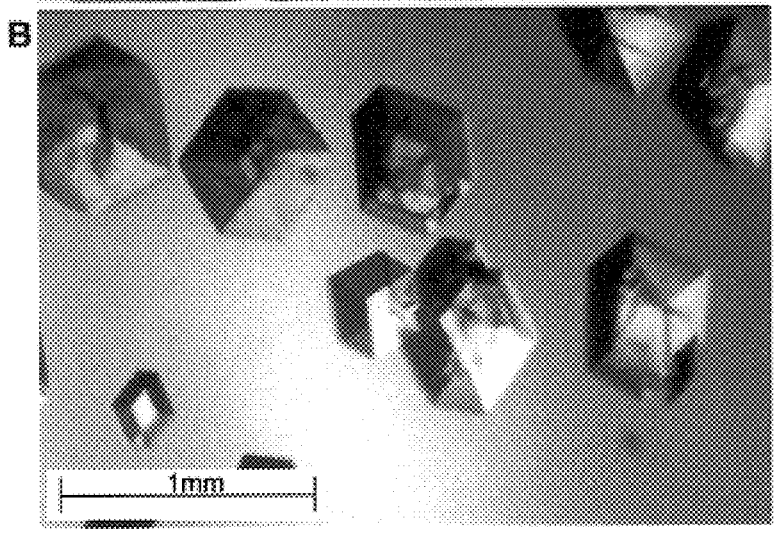

Overall, the microgravity-grown crystals were larger and contained fewer visible flaws than their earth-grown counterparts seen in FIG. 11. The majority of the earth-grown crystals had sedimented to the bottom of the growth chamber and grew as clusters of many crystals. Most of the large earth crystals were clustered. The best looking, single crystals were chosen for mounting. The population of microgravity crystals consisted of many large, single crystals. It is believed that the lack of crystal clusters for the microgravity samples was because the crystals did not sediment during growth in microgravity. The microgravity crystals for study were chosen at random—if anything the study was biased in favor of the earth crystals. Visually flawless crystals, six from microgravity and six from earth, were mounted in 1 mm quartz glass capillaries. The diffraction statistics are shown in FIG. 12 (Table 5). The larger microgravity crystals were mounted near the bell of the capillary. Three crystals of each type were mounted and exposed in the first data collection period, approximately 1 month after the return of the mission, the remaining six crystals were mounted and exposed approximately 6 months later. Crystals were stored in their original growth hardware at 22° C. until they were used. During data collection, the crystals were kept at 22° C. with a regulated gas stream.

The following data collection stategy was used. To determine the crystal orientation, two orthogonal 8–10° swaths were collected ($\Delta\Phi=1°$ with 60 s exposure) and processed with MOSFLM (Powell, 1999). Then, from each swath a 1.0° image was selected and superfine $\Phi$ sliced data (stills spaced by 0.001° with 2 or 5 s exposure time depending on the diffraction strength of the crystal) corresponding to that image were collected for mosaicity measurements. The crystal to detector distance was 170 mm and the beam was collimated to 0.3 mm in diameter. The space group was R3 was cell dimensions a=b=82.8, c=34.2 Å.

The reflections were profiled in the phi (rotation) dimension as described herein in Example I. It was not feasible to profile the reflections in additional dimensions from the spot shape on the detector because the detector resolution was inadequate. Under the conditions used, each detector pixel subtended more than 0.054°, more than 50 times the resolution obtained in the phi dimension.

Data Processing: Data was processed using the BEAM-ish program, according to the present invention, and the true crystal mosaicity ($\eta$) was deconvoluted from the measured reflection full width at half maximum ($\Phi_R$) as described in Example I. Data from the earth-grown crystals were much weaker overall than the data from the microgravity-grown crystals. To reduce noise the earth data were smoothed by averaging the data in a 0.003° window. This was not necessary for the microgravity data. In order to be accepted for profile analysis the reflections from the earth crystals had to have $I_{max}>100$ and $I_{max}/I_{ave}>5$. For the microgravity crystal the thresholds were more stringent with $I_{max}>150$ and $I_{max}/I_{ave}>10$. In both cases $I_{ave}$ was defined as the average of all the integrated spot intensities at the reflection's location measured during the fine phi collection after removal of the "zingers". Zingers are signals produced in the detector by cosmic rays or radioactive decay. This is clearly not the standard method of obtaining accurate reflection intensities but it is computationally simple and suffices to identify the reflections strong enough to provide statistically reliable data.

Figure 13:
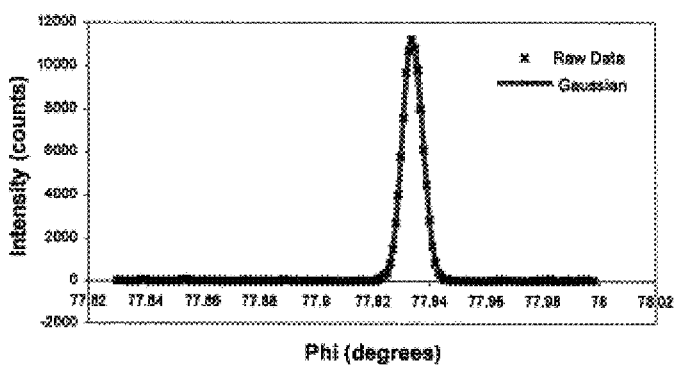
FIGS. 13a and b are graphs that show typical reflection profiles for (a) the [−14, −9, −2] reflection from crystal μg-4 ($\Phi_R$=0.010°, η=0.004°), and (b) [5, −16, 3] reflection from crystal earth-5 ($\Phi_R$=0.036°, η=0.010°, see FIG. 12 (Table 5)).
Figure 13:
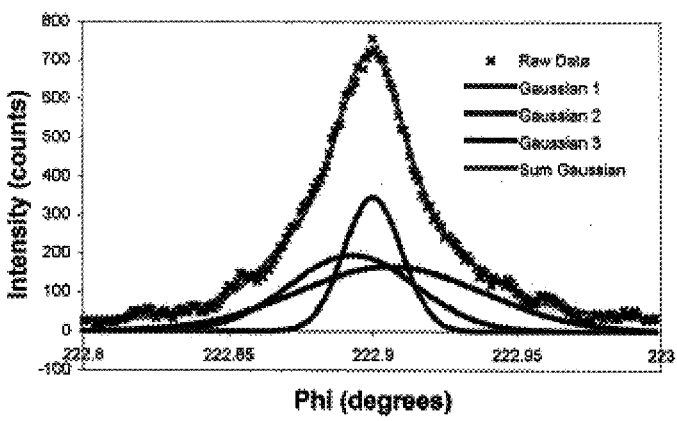

When compared to their earth-grown counterparts, microgravity-grown crystals are extremely well ordered. Reflection profiles from microgravity crystals were best fit by a single Gaussian function whereas earth crystals required several Gaussians (FIG. 13). Therefore, the microgravity crystals appear to be best described as composed primarily of one resolvable mosaic domain and the earth crystals of several domains. This improvement in internal order was found in all microgravity samples studied.

Figure 14A:
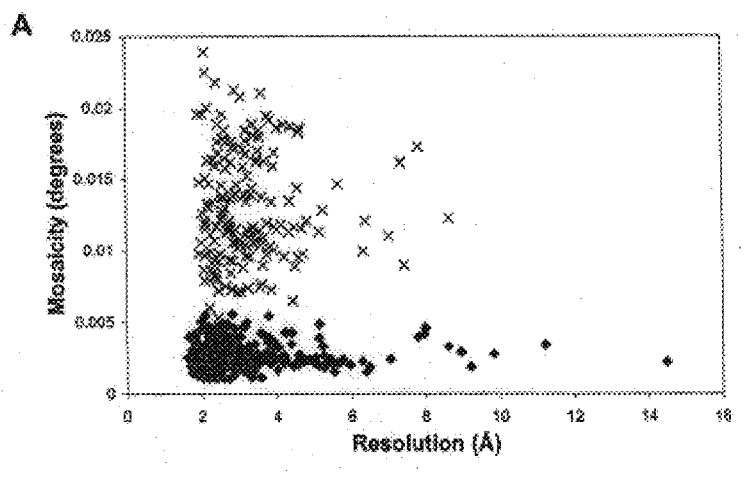
FIGS. 14a and b are graphs showing the crystal quality comparison of the most perfect microgravity (μg-4, blue diamonds) and earth crystals (earth-5, red crosses) by plotting individual reflection FIG. 14(a) mosaicity.
Figure 14B:
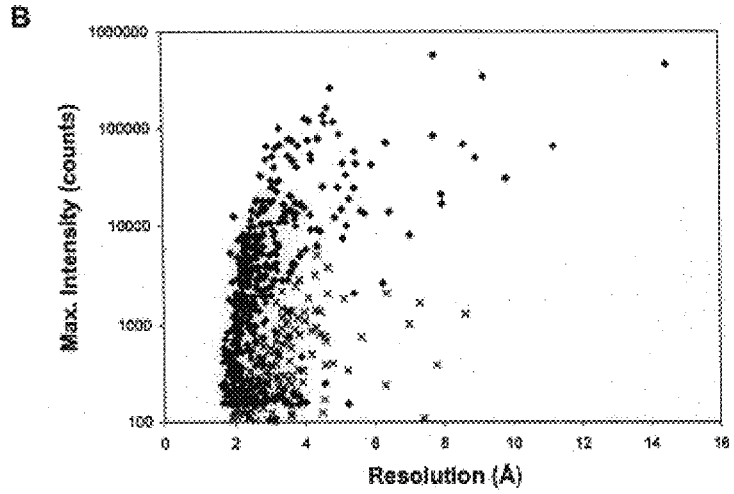
FIG. 14(b) background-subtracted, maximum intensity against resolution. The data were cutoff at the detector edge. For the microgavity crystals the data extended beyond this limit. Maximum intensity normalized to 2 second X-ray exposure is plotted on a log scale.

The microgravity crystals diffracted strongly and between 447 and 502 reflections were profiled in two degrees of superfine $\Phi$ sliced data. This is to be compared with 14 to 174 reflections profiled in equivalently accumulated data from the earth crystals, as seen in FIG. 12 (Table 5). The disparity in the numbers of reflections profiled is due to the relative paucity of reflections strong enough to be accurately profiled in the earth data. Overall, microgravity crystals were of very similar quality whereas the quality of the earth crystals varied significantly (Table 5). The best microgravity crystals ($\mu$g-4 and $\mu$g-6) had an average $\eta$ of 0.002° and 0.003°, respectively, each with a standard deviation of only 0.001°. It is noteworthy that these values are near the limit of resolution of the instrument configuration used. Two of the earth crystals (earth-5 and earth-3) had fairly good mosaicity with average $\eta$ values of 0.013° (s.d. 0.004°) and 0.017° (s.d. 0.005°), respectively, yet these $\eta$ values were 6.5 and 8.5 times higher than the best microgravity crystals and both crystals were relatively poor diffractors (see FIG. 12 (Table 5) and FIG. 14b). For any given earth crystal, the $\eta$ values for individual reflections varied over a surprisingly large range, with standard deviations of 0.004 to 0.024°. The spread in $\eta$ for microgravity crystals was 4–5 fold narrower with standard deviations ranging from 0.001 to 0.005°. It is noteworthy that three of the earth-5 $\eta$ values overlap with the $\mu$g-4 reflections (FIG. 14). This illustrates the importance of collecting a statistically significant number of reflections from each sample in that if only these three reflections had been measured the samples would have been falsely concluded to be indistinguishable. A students t-test on the microgravity and ground mosaicity values showed normal distributions but unequal variance in the two populations. This is reflected in the greater standard deviations for the earth data. A non-parametric, distribution free, Mann-Whitney rank sum test confirms that the microgravity and the earth data are statistically different from each other at the 99% confidence interval (T=57, p=0.002). It is important, not only to collect a statistically significant number of reflections but also to collect from a statistically significant number of samples.

The improvement in internal order in combination with the increase in the volume of crystal illuminated by the synchrotron beam resulted in dramatically more intense diffraction from the microgravity crystals. For example, the microgravity crystal with the best mosaicity, $\mu$g-4, was 23 times larger than the best earth crystal, earth-5, which had 6.5 times lower mosiacity and had 54 fold higher reflection peak heights (FIG. 14b, and FIG. 12 (Table 5)). The largest earth crystal, earth-1, had 24 fold lower reflection peak heights and 7.8 fold higher mosaicity and was 6.3 times smaller than the smallest microgravity crystal studied, $\mu$g-3. The worst microgravity crystal, $\mu$g-2, had 2.2 times lower mosaicity than the best earth crystal, earth-5, but it was 21 times larger and had reflection peak heights that were 33 fold higher. The earth crystals were fully immersed in the beam whereas the larger microgravity crystals were only partially illuminated. This makes it difficult to quantitatively compare diffraction strength, but, while microgravity crystals were significantly larger than the earth-grown counterparts, the increase in the maximum reflection peak height from the microgravity crystals is greater than the increase in the illuminated volume of the crystal. There is no evidence for any handling problems during the mounting as evidenced by the normal distribution of the results and two clear sample populations. The lack of sample degradation between the two synchroton runs is shown in FIG. 12 (Table 5). Storage in the original growth container at the growth temperature seems adequate for insulin.

Results: The first studies showing that microgravity reduces mosaicity (Snell et al., 1995; Ng et al., 1997) were confirmed. The diffraction signals from the microgravity crystals were much cleaner than from the earth crystals (FIG. 13 and FIG. 14)) due to the reduction in mosaicity. Microgravity can provide an environment where large, internally well-ordered crystals can be grown. Such crystals provide better spatial resolution, less spot overlap and a higher signal-to-noise ratio. Large unit cells with spatial overlap problems, Laue studies, emerging ab initio phasing technologies that require accurate intensity data, such as sulfur anomalous scattering (Wang, 1985), or require low mosaicity, such as triplet-phase measurements using reference-beam X-ray diffraction (Shen et al., 2000, Weckert et al., 1997), will benefit significantly from such high quality crystals.

Large crystals of macromolecules are often imperfect, which results in poor diffraction quality. Partly because of this, the current trend is to collect data from small crystals using synchrotron radiation. Microgravity appears to be able to break the common inverse relationship between crystal size and crystal quality. It may also enable diffraction quality crystals to be grown where previously only microcrystals could be obtained. Excellent crystals of large volume will enable more samples to be studied using neutron diffraction. Neutron studies require large volume crystals, >1 mm$^3$, due to the weak scattering and low beam intensity. In addition, when the Laue method is used, reflection overlap is a problem that can be greatly reduced with low moasaicity. This last requirement is essential for samples with large unit cells.

In this case, microgravity had a dramatic effect on the size and physical perfection of insulin crystals grown by a temperature-regulated batch method. It is noteworthy that the growth method employed essentially eliminates the Maragoni convection that in principle affects other growth methodologies. Six crystals from microgravity and six from earth were studied. The results from microgravity and earth were self-consistent and distinct. Each result is based on many individual reflections. In this case, microgravity passed the test.

EXAMPLE III

Crystallization of lysozyme in microgravity took place on the US Space Shuttle STS-95 mission. This nine-day mission was launched on Oct. 29$^{th}$, 1998. Crystals were grown by liquid-liquid diffusion in the Dual Materials Dispersion Apparatus (DMDA) (Instrumentation Technology Associates). The DMDA is a multiwell apparatus of a sliding block design. The top and bottom wells of each experiment contained 122 μl of 7% w/v NaCl solution and 105 μl of 7% w/v lysozyme solution, respectively. The equilibrium precipitant concentration was 3.76%. Both salt and protein solutions also contained 0.1 M sodium acetate buffer at pH 4.8. Initially separated, the experiment was activated after reaching low Earth orbit by bringing both wells into alignment. This allowed the solutions to diffuse into each other across a liquid-liquid interface. Experiments were conducted at 20° C. and contained various added concentrations of the lysozyme dimer. Approximately 6 hours after landing the crystals were harvested from the DMDA using the existing mother liquor. The wells were then rinsed with an artificial mother liquor to recover any remaining crystals. Crystal samples were returned to the University of Colorado at Boulder then transported in large capillary tubes to NASA, Marshall Space Flight Center (MSFC), where they were stored at 22° C.

The ground crystallization experiments were conducted in 96-well plates at the same temperature and using the same solutions as used in the microgravity mission. In an attempt to mimic the liquid-liquid interface diffusion experiments conducted in microgravity, the same solution volumes and concentrations were used. The precipitant solution was placed first in the well and the protein solution was gently over layered on top of it. The plate was sealed with transparent tape and incubated for a similar time period to that used in the mission. Crystallization experiments conducted at different precipitant concentration were performed in the same way with the same initial supersaturation (ln(c/s)= 2.25, where c is the bulk solution concentration and s is the solubility) and initially contained 3.6% (w/w) dimer.

X-ray analysis. The experimental setup for measuring crystal mosaicity and diffraction resolution using unfocused monochromatic synchrotron radiation in combination with superfine slicing was as described in the previous examples. Crystals were mounted in quartz glass capillaries and data were collected at 22° C. Temperature was controlled by a regulated nitrogen gas stream. The coarse data were processed with MOSFLM and reduced with CCP4 packages. For each crystal two orthogonal swathes of coarse (ΔΦ=1°) and superfine (ΔΦ=0.001°) X-ray diffraction data were collected as shown in FIG. 15 (Table 5). The superfine Φ sliced data were processed to evaluate the reflection profiles and deconvolute Lorentz, geometrical and spectral effects using the program Beamish of the present invention. Reference J. Appln. Cryst. Lovelace et al. A signal to noise cutoff of 5 σ was used and negative mosaicities were discarded as partials.

FIG. 15 (Table 6) shows experimental data collection parameters and crystal sizes. The size was evaluated by measuring the largest dimension then the other two perpendicular dimensions. For each crystal two 10° swaths of coarse data with ΔΦ=1° were collected 90° apart. Two 1° swaths of superfine sliced data as 0.001° separated stills were then collected. For the ground 3.6% case swathes were collected 45° apart. The space group for all crystals was $P4_32_12$.

Anisotropic Mosaicity Calculation. Ferrer et al., 1998, described a mosaicity model in terms of the crystallographic directions h, k and l. This model was reformulated for the general case as follows:

$$\eta_{hkl}^{calc} = \frac{\eta_{abc}\left(\frac{(ah)^2 + (bk)^2 + (cl)^2}{a^2 + b^2 + c^2}\right) + \eta_{def}\left(\frac{(dh)^2 + (ek)^2 + (fl)^2}{d^2 + e^2 + f^2}\right) + \eta_{mno}\left(\frac{(mh)^2 + (nk)^2 + (ol)^2}{m^2 + n^2 + o^2}\right)}{h^2 + k^2 + l^2} + \eta_{const}$$

where (a,b,c), (d,e,f) and (m,n,o) define Bragg planes. The model was fit to the measured deconvoluted mosaicity data using a multivariate regression analysis. Two sets of planes were fit to the data, one along the crystallographic axes (1,0,0), (0,1,0) and (0,0,1) after Ferrer et al., supra, and the other along the growth directions of the crystals (1,1,0), (1,0,1) and (0,1,1). The isotropic component, $\eta_{const}$, was set to zero. A sample coefficient of multiple determination, $R^2$, (where $R^2 \times 100\%$ is the percentage of the data that can be fitted with the model) of the model was calculated to describe the goodness of fit. The data were fitted to several Gaussians with the assumption of a linear background.

FIG. 16 (Table 7) shows the anisotropic refinement of mosaicities. $R^2$ is the goodness of fit of the anisotropic mosaicity. The number of Gaussians fitted to the data is also noted with the % of reflections fitted. For the 0% dimer earth sample the two swaths of data collected were fitted to one and two Gaussians, respectively. The average mosaicity for each Gaussian is noted with the standard deviation in brackets, both in thousandths of a degree. Due to differences in exposure times (FIG. 5, Table 6) it is inappropriate to compare the number of reflections between crystals. .Note, only 1° of data was collected for the 0.9% superfine sliced data in comparison with 20° for the rest of the data.

The directional components of crystal mosaicity, analyzed using an anisotropic model as described in Example I above. FIG. 16, (Table 7), shows that when dimer concentration is increased mosaicity seen in the h direction, $\eta_h$, increases with dimer content becoming maximum at the 1.8% level (four times that of the pure crystal). This is also seen in $\eta_k$ where the 1.8% impurity has twice the mosaicity of the pure crystal. For this space group, $P4_32_12$, we would expect that the h and k mosaicities would be the same unless the crystal has macroscopic defects. The microgravity crystal, grown in a reduced sedimentation environment, should be even more symmetric. Differences between $\eta_h$ and $\eta_k$ are probably a measure of the uncertainty in the data. In the l direction the mosaicity, $\eta_l$, maximizes at the 0.9% impurity level. The largest decrease in mosaicity occurs for $\eta_l$, in both the 3.6% impurity ground and microgravity samples. The goodness-of-fit values are low, however, suggesting that a 3 dimensional anisotropic refinement as a function of h, k and l, is not a suitable model for the system. A similar trend in mosaicity is seen with the anisotropic fit to the growth directions of the crystal but again not well fit by this model. Crystal growth occurs over a period of hours with changing solution conditions due to the incorporation of protein from the solution into the crystal. The crystal is therefore an integration of the crystallization process over time, and it is perhaps not surprising that there is not a good fit to these simple models. The fit is worst for the 0, 0.5 and 0.9% microgravity crystals, suggesting that these are more isotropic than anisotropic, a result consistent with the study of microgravity grown insulin crystals. The best fit using an anisotropic model was 0.3 for Mn Super Oxide Dismutase (Example I above, i.e. only 30% of the data could be accurately fitted with the model used).

Also shown in FIG. 16 (Table 7) are the number of reflections and percentages fitted by numbers of Gaussians. The width of the Gaussian, with standard deviation in thousandths of a degree is also given. Most samples are best fitted by two Gaussians. The 1.8% dimer microgravity sample is best fitted with three and the 0% earth fitted with a single Gaussian for one swath of data but two for the other. It is noticeable with the mosaicity values of the Gaussians that, in the microgravity case, there is an increase to a maximum Gaussian width and number at 1.8% followed by a falloff to two narrower Gaussians at greater impurity. The large value for the third Gaussian in the 1.8% microgravity case indicates it is made up of many smaller domains that are not resolved.

EXAMPLE IV

During the analysis of the MnSOD crystal data two Gaussians were automatically fit to all reflections, It was noted that in the vertical sectors of the detector the fitting seemed to be well behaved and their centroids made sense in terms of the width of the deconvoluted true crystal mosaicity. In the horizontal sectors, where the reflections are broadened significantly by the Lorentz effect and the horizontal beam divergence, the center of the Gaussians was less accurate. A Fourier deconvolution of the data before fitting Gaussians or measuring the profile width alleviates this problem. The measured data is a convolution of the instrument effects with the true sample profile. Deconvoluting out the instrument effects can be achieved with Fourier methods using the relationship: $F(\overline{\omega})=G(\overline{\omega})/I(\overline{\omega})$, where $F(\overline{\omega})$, $G(\overline{\omega})$ and $I(\overline{\omega})$ are the Fourier transforms of the true sample profile, the measured profile and the instrument function, respectively.

This invention is not limited to the determination of the diffraction resolution and mosaic spread of a protein crystal.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments described explain the principles of the invention and practical applications and should enable others skilled in the art to utilize the invention in various embodiments and with various modifications as are suited to the particular use contemplated. It is intended that the scope of the invention be defined by the claims appended hereto.

The following references to the extent that they provide exemplary procedural or other details supplementary to those set forth herein, are specifically incorporated herein by reference.

REFERENCES

Baker, E. N., et al. (1988). *Phil. Trans. R. Soc. Lond. B*319, 369–456.
Boggon, T. J., et al. (2000) *Acta Cryst.* D56, 868–880.
Borgstahl, et al. (2000), *J. Mol. Biol.* 296, 951–959.
Chayen, N. E., et al. (1997). *J. Cryst. Growth* 171, 219–225.
Ciszak, E. et al. (1994). *Biochemistry* 33, 1512–1517.
Colapietro, M., et al. (1992) *J. Appl. Cryst.* 25, 192–194.
Collaborative Computational Project, Number 4 (1994) *Acta Cryst.* D50, 760–763.
Darwin, C. G. (1922). Philos. Mag. 43, 800–829.
Evans, P. R. (1997). *In Proceedings of the CCP4 Study Weekend. Recent Advances in Phasing*, edited by K. S. Wilson, G. Davies, A. W. Ashton & S. Bailey. Warrington: Daresbury Laboratory.
Ferrer, J. L., et al. (1998) *J. Appl. Cryst.* 31, 523–532.
Fourme, R., et al. (1995) *J. Synchrotron Rad.* 2, 136–142.
Greenhough, T. J., et al. (1982). *J. Appl. Cryst.* 15, 338–351.
Helliwell, J. R. (1988), *J. Cryst. Growth,* 90, 259–272.
Helliwell, J. R. (1992) *Macromolecular Crystallography with Synchrotron Radiation.* Cambridge University Press.
Kabsch, W. (1988). *J. Appl. Cryst.* 21, 916–924.
Leslie, A. G. W. (1990) *Crystallographic Computing,* edited by V. D. Moras, A. D. Podjarny & J. C. Theirry, pp.27–38. Oxford University Press.
Leslie, A. G. W. (1999). *Acta Cryst.* D55, 1696–1702.
Long, M. M., et al. (1996). *J. Crystal Growth* 168, 233–243.
Margaritondo, G. (1995) *J. Synchrotron Rad.* 2, 148–154.
Nave, C. (1998). *Acta Cryst.* D54, 848–843.
Nave, C. (1999). *Acta Cryst.* D55, 1663–1668.
Ng., J. D., et al. (1997). *Acta Cryst.* D53, 724–733.
Powell, H. R. (1999). *Acta Cryst.* D55, 1690–1695.
Pusey, M. L., et al. (1986). *J. Biol. Chem* 261, 6524–6529.
Pusey, M., et al. (1988). *J. Cryst. Growth* 90, 105–111.
Shaikevitch, A., et al. (1981). *Acta Cryst.* A37, 871–875.
Shen, Q. et al. (2000). *Acta Cryst.* A56, 268–279.
Snell, E. H., et al. (1995). *Acta Cryst.* D51, 1099–1102.
Snell, E. H. (1998). *Proceedings of the Spacebound 1997 Meeting,* pp. 306–315. Canadian Space Agency.
Snell, E. H., et al. (1997). *Acta Cryst.* D53, 231–239.
Steller, I., et al. (1997). *J. Appl. Cryst.* 30, 1036–1040.
Wang, B. C. (1985). *Methods in Enzymol.* 115, 90–112.
Weckert, E. et al. (1997). *Acta Cryst.* A53, 108–143.

The embodiment of this invention in which an exclusive property or privilege is claimed is defined as follows:

We claim:

1. A method to simultaneously measure diffraction resolution and mosaic spread of a macromolecular crystal including the steps of (a) minimizing contributions of an x-ray beam to any reflection angular widths in the crystal by using a highly parallel, highly monochromatic x-ray source;

(b) rapidly measuring multiple reflection profiles in the crystal over a wide resolution range using a suitable fast readout area detector in combination with superfine oscillation Φ-slicing imaging data collection; and (c) evaluating and deconvoluting the Lorentz effect and beam contributions from the recorded data.

2. The method of claim 1, further including:

(d) determining the direction in which the crystal is most imperfect.

3. The method of claim 2, further including:

(e) measuring accurate intensities through file slicing, deconvolution and profile fitting.

4. The method of claim 1, in which the superfine oscillating Φ slice data is collected on a crystal.

5. The method of claim 4, in which multiple reflection profiles are measured as the full-width at half-maximum (FWHM) or as the full width at quarter maximum (FWQM).

6. The method of claim 5, which each reflection profile is fitted with at least one mathematical function that fits the recorded data.

7. The method of claim 6, in which the mathematical function is at least one Gaussian profile.

8. The method of claim 6, in which the mathematical function is at least one Lorentzian profile.

9. The method of claim 1, in which the fast readout area detector is composed of a charge coupled device(s).

10. The method of claim 4, in which from about 0.0001° to about 1° of the super fine oscillation data is collected.

11. The method of claim 1, in which mosaicity is determined from the measured reflection widths using formula $$\eta = \frac{|\varphi_R| - (L^2 \zeta^2 \gamma_h^2 + \gamma_v^2)^{\frac{1}{2}}}{(L/d)\cos\theta_{hkl}} \left(\frac{\delta\lambda}{\lambda}\right)\tan\theta_{hkl}.$$

12. The method of claim 1, which the diffraction data are processed by (a) indexing and integrating the 1° oscillation images using MOSFLM and scaling of data with suitable software to provide statistics on crystal quality, including the agreement between symmetry-related reflections Rsym and the signal-to-noise ratio 1/σ(I);

(b) using an orientation matrix to integrate the coarse oscillation image that corresponds with the superfine Φ-sliced images;

(c) obtaining a reflection profile from the crystal by integrating the super fine Φ-sliced data;

(d) removing random radiation events from the diffraction data;

(e) locating the Φ position of the maximum value of the reflection;

(f) calculating the width of the reflection as full width half-minimum (FWHM) and full-width at quarter-minimum (FWQM) and true crystal mosaicity η; and (g) fitting one or more mathematical functions that fit the data to all the reflection profiles.

13. The method of claim 3, in which step (g) comprises fitting the at least one mathematical function to the reflection profile wherein lmax/lbkg is greater than an arbitrary value including where lmax/lbkg>1–10.

14. The method of claim 13, in which the mathematical function is at least one Guassian profile.

15. The method of claim 13, in which the mathematical function is at least one Lorentzian profile.

16. The method of claim 13, in which a suitable signal-to-noise ratio is used to filter out noise.

17. The method of claim 12, in which the reflection list includes indices for each reflection along with its detector coordinates for each reflection and the estimated error for each reflection.

18. The method of claim 12, in which 0.001° images are integrated at the reflection coordinate positions for reflections with a desired signal-to-noise ratio.

19. The method of claim 12, in which, in step (g), two Gaussian functions are used.

20. The method of claim 19, in which the initial Gaussians are placed as follows before a fitting algorithm is employed: a first Gaussian function is placed at the maximum and a second Gaussian function is placed at the FWQM value to the right or left of the maximum by comparing the ratio of FWHM to FMQM for each side with that of a perfect Gaussian.

21. The method of claim 12, in which the quality of the crystal is quantitatively analyzed by examining the reflection profiles recorded near a vertical equatorial axis.

22. The method of claim 12, in which the relative contributions of domain misalignment and volume are distinguished from a variation of d spacing within a domain by analyzing mosaicity as a function of resolution.

23. The method of claim 12, in which angular separation between multiple peaks are used to measure misalignment of discrete domains.

24. The method of claim 12, which an anisotropic η calculation is applied to each individual mathematical function that were fit to the data profiles.

25. The method of claim 12, in which the measured mosaicity is used to identify types of imperfections existing with the crystal.

26. A method for comparing different samples of crystals using symmetry related reflections obtained by using the method of claim 1.

27. A method for comparing different samples of crystals using symmetry related reflections obtained by using the method of claim 6.

28. The method of claim 6, in which the step (e) of the accurate positioning of the maximum of the reflection allows for the increased accuracy in orientation matrix resulting in more accurate cell parameters.

29. The method of claim 1, in which at least one Gaussian functions or other mathematical function is used.

30. The method of claim 7, in which the Gaussian profile(s) is fit to the recorded data and deconvoluted using $$\eta = \frac{|\varphi_R| - (L^2 \zeta^2 \gamma_h^2 + \gamma_v^2)^{\frac{1}{2}}}{(L/d)\cos\theta_{hkl}} \left(\frac{\delta\lambda}{\lambda}\right)\tan\theta_{hkl}.$$

31. The method of claim 14, in which the Gaussian profile(s) is fit to the recorded data and then deconvoluted using $$\eta = \frac{|\varphi_R| - (L^2 \zeta^2 \gamma_h^2 + \gamma_v^2)^{\frac{1}{2}}}{(L/d)\cos\theta_{hkl}} \left(\frac{\delta\lambda}{\lambda}\right)\tan\theta_{hkl}.$$

32. The method of claim 7, in which a Fourier deconvolution is used to remove inaccuracies in any broad reflection, and then fitting the mathematical functions to the data profile.

33. The method of claim 32, in which the formula F(ω)=G(ω)/I(ω) is applied where F(ω),G(ω), and I(ω) are the Fourier transforms of the true sample profile, the measured profile and the instrument function, respectively.

* * * * *

UNITED STATES PATENT AND TRADEMARK OFFICE
CERTIFICATE OF CORRECTION

PATENT NO. : 6,498,829 B1
DATED : December 24, 2002
INVENTOR(S) : Gloria E.O. Borgstahl, Jeffrey J. Lovelace and Edward H. Snell It is certified that error appears in the above-identified patent and that said Letters Patent is hereby corrected as shown below:

<u>Column 1,</u>
Line 5, please add the following paragraph:
-- This invention was made with Government support under grant NAG8-1380 awarded by NASA. The Government has certain rights in this invention. --

Signed and Sealed this

Fourteenth Day of September, 2004

JON W. DUDAS
*Director of the United States Patent and Trademark Office*